(12) United States Patent
Andretta

(10) Patent No.: US 12,214,157 B2
(45) Date of Patent: Feb. 4, 2025

(54) FLUID INTERFACE DEVICE FOR DELIVERING FLUID TO AND/OR WITHDRAWING FLUID FROM A PATIENT

(71) Applicant: SeraIP AG, Stans (CH)

(72) Inventor: Carlo Andretta, Uitikon-Waldegg (CH)

(73) Assignee: SeraIP AG, Stans (CH)

( * ) Notice: Subject to any disclaimer, the term of this patent is extended or adjusted under 35 U.S.C. 154(b) by 0 days.

(21) Appl. No.: 17/465,880

(22) Filed: Sep. 3, 2021

(65) Prior Publication Data
US 2022/0054749 A1 Feb. 24, 2022

Related U.S. Application Data

(63) Continuation of application No. 16/060,963, filed as application No. PCT/EP2016/080694 on Dec. 12, 2016, now Pat. No. 11,110,222.

(30) Foreign Application Priority Data

Dec. 11, 2015 (EP) ...................................... 15199669
Jun. 28, 2016 (EP) ...................................... 16176765
Jun. 28, 2016 (EP) ...................................... 16176771

(51) Int. Cl.
*A61M 5/142* (2006.01)
*A61B 5/15* (2006.01)
(Continued)

(52) U.S. Cl.
CPC ......... *A61M 5/14276* (2013.01); *A61B 5/157* (2013.01); *A61M 5/1723* (2013.01);
(Continued)

(58) Field of Classification Search
CPC ............ A61M 5/1723; A61M 5/14276; A61M 39/0208; A61M 39/10; A61M 2039/0276;
(Continued)

(56) References Cited

U.S. PATENT DOCUMENTS 4,704,029 A 11/1987 Heuvelen
5,324,518 A 6/1994 Orth et al.
(Continued)

FOREIGN PATENT DOCUMENTS

CN 101415460 A 4/2009
CN 202069931 U 12/2011
(Continued)

OTHER PUBLICATIONS

Federal Service on Intellectual Property (Russia), Search report issued for appl. no. 2018125067 (counterpart RU application) on Feb. 17, 2020 (English translation provided).
(Continued)

*Primary Examiner* — James D Ponton
(74) *Attorney, Agent, or Firm* — Agris & von Natzmer LLP; Joyce von Natzmer

(57) ABSTRACT

A fluid interface device for delivering fluid to and/or withdrawing fluid from a patient, the device comprises a peripheral base element (2) and a fluid transmission element (4) sealingly connected to the base element and forming a central portion of the device. The fluid transmission element comprises a front platelet (6) with a primary face (8) and a secondary face (10) opposed thereto, the primary face being in contact with a patient's body fluid region (12) when the device is implanted in the patient, the fluid transmission element further comprising a counterplate (14) sealingly stacked against the secondary face of the front platelet and forming a buffer volume (16) therebetween. The front platelet comprises at least one array of microchannels (18) defining a fluid passage between the buffer volume and the primary face, the microchannels having an opening of 0.2 to 10 μm. The counterplate has at least one fluid port (20; 20*a*, 20*b*) for fluid delivery to and/or fluid withdrawal from the buffer volume.

37 Claims, 15 Drawing Sheets

(51) Int. Cl.
  *A61B 5/157* (2006.01)
  *A61M 5/172* (2006.01)
  *A61M 39/02* (2006.01)
  *A61M 39/10* (2006.01)

(52) U.S. Cl.
  CPC ........ *A61M 39/0208* (2013.01); *A61M 39/10* (2013.01); *A61B 5/15003* (2013.01); *A61M 2039/0276* (2013.01); *A61M 2230/201* (2013.01)

(58) Field of Classification Search
  CPC ........ A61M 2230/201; A61M 39/0247; A61B 5/157; A61B 5/15003
  See application file for complete search history.

(56) References Cited

U.S. PATENT DOCUMENTS

| | | | |
|---|---|---|---|
| 6,379,324 B1* | 4/2002 | Gartstein | A61B 5/150458 604/20 |
| 6,689,100 B2* | 2/2004 | Connelly | A61M 37/0015 604/289 |
| 7,621,905 B2 | 11/2009 | Penner et al. | |
| 9,023,292 B2 | 5/2015 | Rostaing et al. | |
| 11,110,222 B2* | 9/2021 | Andretta | A61M 5/1723 |
| 2003/0049865 A1 | 3/2003 | Santini et al. | |
| 2005/0096516 A1* | 5/2005 | Soykan | G01N 21/6428 600/317 |
| 2006/0071362 A1 | 4/2006 | Yeung et al. | |
| 2009/0076453 A1 | 3/2009 | Mejlhede et al. | |
| 2009/0221971 A1 | 9/2009 | Mejlhede et al. | |
| 2010/0042070 A1 | 2/2010 | Gill et al. | |
| 2010/0256466 A1 | 10/2010 | Shekalim et al. | |
| 2013/0053671 A1 | 2/2013 | Farra | |
| 2014/0276466 A1 | 9/2014 | Yeh et al. | |
| 2015/0283366 A1 | 10/2015 | Zumbrunn et al. | |

FOREIGN PATENT DOCUMENTS

| | | |
|---|---|---|
| CN | 102639183 A | 8/2012 |
| CN | 104271180 A | 1/2015 |
| EP | 2455119 A1 | 5/2012 |
| FR | 2923151 B1 | 9/2010 |
| GB | 2517707 A | 3/2015 |
| JP | 2005527254 A | 9/2005 |
| JP | 2008512282 A | 4/2008 |
| RU | 2131270 C1 | 6/1999 |
| RU | 2419460 C2 | 5/2011 |
| WO | 2003030984 A1 | 4/2003 |
| WO | 2007117967 A2 | 10/2007 |
| WO | 2008062173 A1 | 5/2008 |
| WO | 2009071775 A4 | 8/2009 |
| WO | 2011053554 A1 | 5/2011 |
| WO | 2011116388 A1 | 9/2011 |
| WO | 2013171304 A1 | 11/2013 |
| WO | 2015097255 A2 | 7/2015 |

OTHER PUBLICATIONS

Mendis et al. Global status report on noncommunicable diseases 2014, World Health Organization (WHO), Geneva, 2014.

Office Action issued by the Japanese Patent Office in corresponding appl. JP2018549618A (Publ. JP2018537257A) including English translation provided by the Japanese patent agent for applicant, Oct. 20, 2020.

Office Action issued in CN 201680081561.6 on Apr. 28, 2020 including English translation provided by Chinese patent agent for applicant.

Written Opinion that issued for PCT/EP2016/080694 on Jun. 15, 2017.

* cited by examiner

F-F

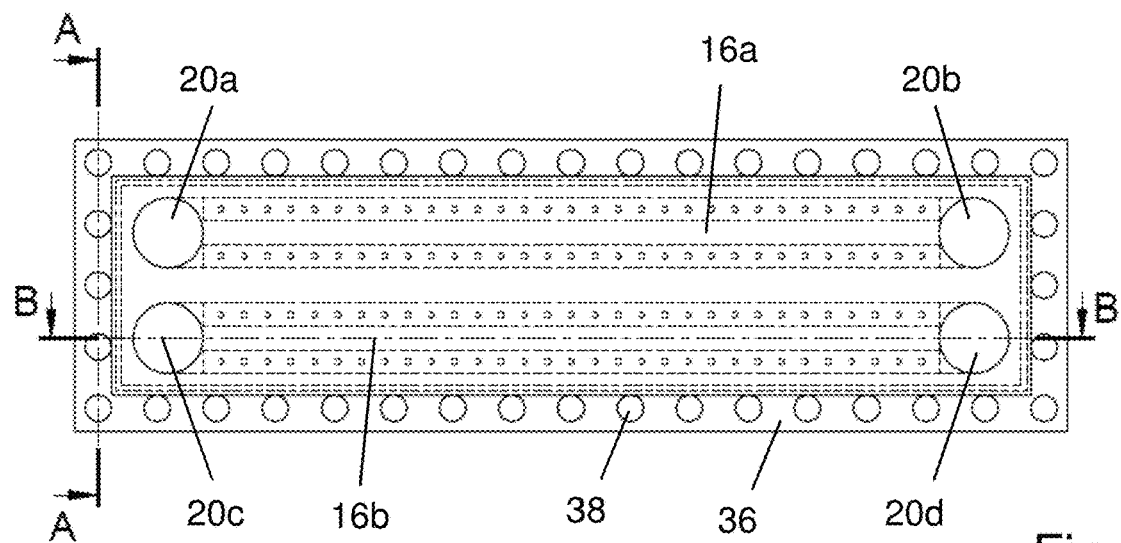
Fig. 8
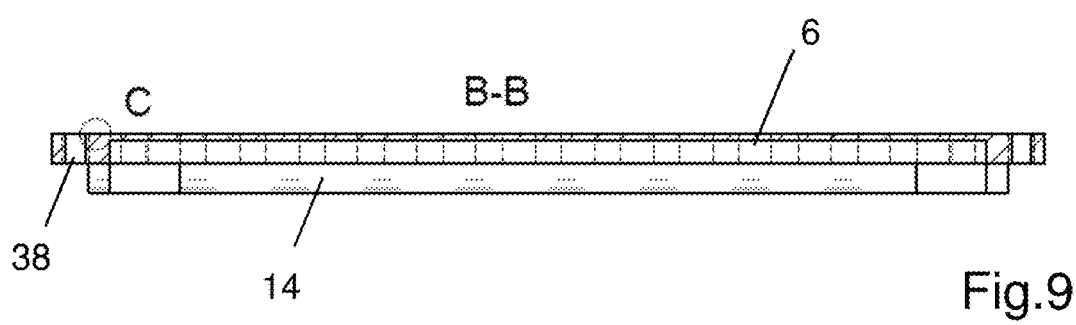
Fig. 9
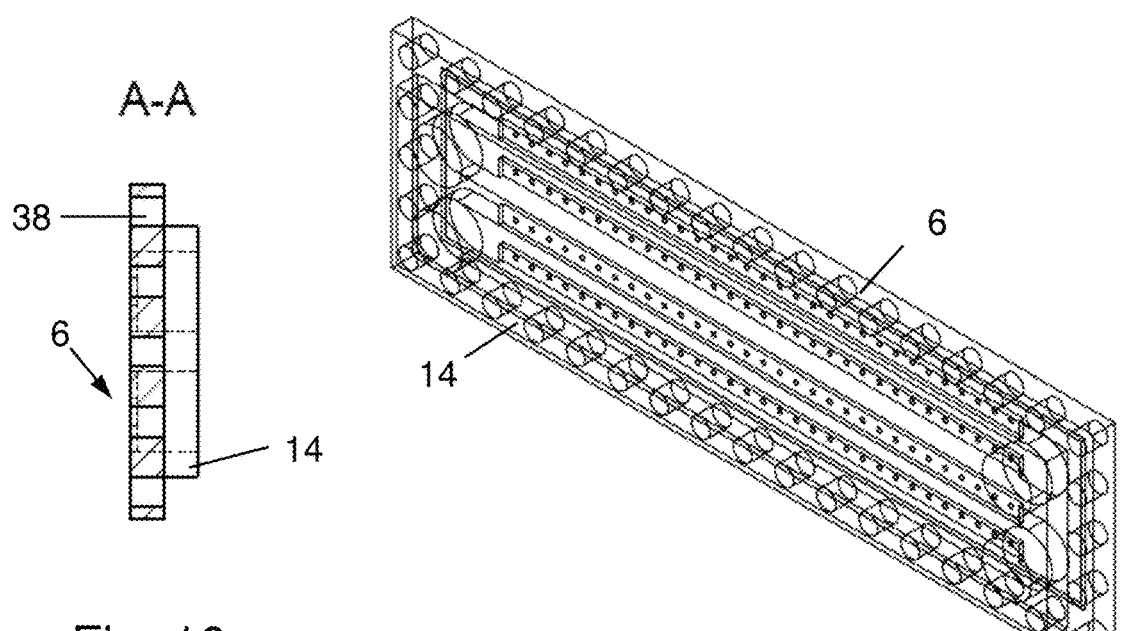
Fig. 10
Fig. 11

FLUID INTERFACE DEVICE FOR DELIVERING FLUID TO AND/OR WITHDRAWING FLUID FROM A PATIENT

CROSS-REFERENCE TO RELATED APPLICATIONS

This is a continuation application of U.S. patent application Ser. No. 16/060,963, which is the US National Stage Entry of international application PCT/EP2016/080694, filed Dec. 12, 2016, claiming priority to European patent application 16176765.2, filed Jun. 28, 2016, European patent application 16176771.0, filed Jun. 28, 2016 and European patent application 15199669.1, filed Dec. 11, 2015 and which applications are incorporated herein by reference in their entireties.

FIELD OF THE INVENTION

The present invention generally relates to a fluid interface device for delivering fluid to and/or withdrawing fluid from a patient. Moreover, the invention relates to a system for delivering fluid to and/or withdrawing fluid from a patient. Furthermore, the invention relates to a method of operating the system.

BACKGROUND OF THE INVENTION

According to the World Health Organization, in 2014 the global prevalence of diabetes was estimated to be 9% among adults aged 18 or more (Global status report on noncommunicable diseases 2014. Geneva, World Health Organization, 2012). Treatment of diabetes involves lowering blood glucose and the levels of other known risk factors that damage blood vessels. For patients with type 1 diabetes, but also for patients with progressed forms of type 2 diabetes, the necessary interventions include administration of insulin. Because of inevitable variations in external influencing factors and often also because of a lack of discipline, the glucose levels in blood often fluctuate substantially, which can lead to a number of complications of the vascular and nervous systems. For such patients, insulin pumps have gained increasing popularity. Most of these pumps emit insulin continuously at a low-dosage basal rate which can be increased on demand, notably before meals. In order to optimize use of an insulin pump, it is highly desirable to also have a system for continuous or periodic monitoring of the blood glucose level. U.S. Pat. No. 4,704,029 discloses a blood glucose monitor system for use as an implant for controlling an insulin pump, or as a portable device for use by a diabetic for home blood glucose monitoring. The glucose monitor measures the glucose level of blood by utilizing a refractometer which measures the index of refraction of blood adjacent to an interface with a transparent surface of the refractometer, by directing light at the interface to measure the index of refraction of the blood by the amount of radiation reflected by the interface, particularly light incident near the critical angle. A proposed device designed to directly contact the blood comprises an optical interface made of a contacting material with a critical surface tension selected so as to minimize deterioration by antibodies and proteins contained in the blood. One such exemplary material is dichloro-dimethyl-silane, also known as G.E. Dry Film.

FR 2923151 A1 describes a blood sampling device with a fluid interface comprising a peripheral element, a fluid transmission element sealingly connected to the base element and forming a central portion of the device, with the fluid transmission element comprising a front platelet with a primary face and a secondary face opposed thereto.

Further blood glucose monitoring systems have been proposed which are based on obtaining a capillary blood sample from a patient; see for example, WO 2008/062173 A1, WO 2009/071775 A1 and WO 2011/116388 A1. Such systems usually comprise either an agglomerating agent or some kind of fibrous filter for removing blood cells and other particles contained in the blood in order to carry out the glucose measurement on blood plasma. As will be known, the term "blood plasma" denotes the liquid fraction obtained by removing the blood cells and other particles contained in blood.

However, an efficient and reliable blood glucose monitor system for controlling an insulin delivery system should preferably be implantable so as to be able to continuously or periodically sample blood plasma from a venous—or possibly arterial—blood vessel. In spite of many attempts, this task does not seem to have been satisfactorily solved. The apparently obvious approach of implanting some kind of microporous membrane into a blood vessel wall, which would allow extracting blood plasma and keep blood cells and other particles in the blood vessel, faces the problem of very rapid obstruction of the micropores by clot formation.

Accordingly, it would be highly desirable to provide a fluid interface for withdrawing blood plasma from a patient in a continuous, reliable manner over extended periods of time, preferably for several years or even longer. It would be equally desirable to have such a fluid interface for withdrawing other types of a patient's fluids such as cerebrospinal fluid. Moreover, it would also be desirable to use the same fluid interface for delivering appropriate fluids such as therapeutic or prophylactic agents to a patient's bloodstream.

SUMMARY OF THE INVENTION

It is thus an object of the present invention to provide an improved fluid interface device for delivering fluid to and/or withdrawing fluid from a patient. In particular, such a device shall overcome the limitations and disadvantages of presently known devices.

According to one aspect of the invention, there is provided a fluid interface device for delivering fluid to and/or withdrawing fluid from a patient, the device comprising:
  a peripheral base element;
  a fluid transmission element sealingly connected to the base element and forming a central portion of the device, the fluid transmission element comprising a front platelet with a primary face and a secondary face opposed thereto, the primary face being in contact with a patient's body fluid region when the device is implanted in the patient, the fluid transmission element further comprising a counterplate sealingly stacked against the secondary face of the front platelet and forming a buffer volume therebetween; the front platelet comprising at least one array of microchannels defining a fluid passage between the buffer volume and the primary face, the microchannels having an opening of 0.2 to 10 µm;
  the fluid transmission element having at least one fluid port for fluid delivery to and/or fluid withdrawal from the buffer volume.

The core part of the device is constituted by the fluid transmission element, which is formed as a chamber containing a buffer volume. Specifically, the transmission element is configured in a sandwich-like manner with a front platelet having a primary face oriented towards the patient's body fluid region of interest. The front platelet comprises at least one array of microchannels defining a fluid passage between the buffer volume and the primary face. The chamber further comprises a counterplate sealingly stacked against the secondary face of the front platelet and forming the buffer volume therebetween. The fluid transmission element has at least one fluid port for fluid delivery to and/or fluid withdrawal from the buffer volume.

The device of the present invention is generally intended for a achieving a reliable, well defined and uninterrupted transfer of predetermined fluids from or into a patient's body fluid region. Such transfer includes but is not limited to withdrawing blood plasma or cerebrospinal fluid and to delivery of therapeutic or prophylactic agents to various body regions of a patient in need thereof. A highly important task of the device is to achieve a filtering function, i.e. to prevent the passage of cells and other particles through the fluid passage.

As will be described in more detail further below, the optimum size of the microchannels will depend on the particular application. In general it will be selected in the range of 0.2 to 10 µm. The lower limit is primarily determined by the available forming technology, but also by the need to have sufficient throughput. The upper limit is determined by the size of particles that should be prevented from entering into the microchannels. For applications involving the withdrawal of blood plasma the microchannels should have an opening in the range of 0.9 to 2.2 µm, most typically of around 1.6 µm. The term "opening" shall be understood as the diameter in the case of microchannels with circular cross section; for non-circular microchannels the term "opening" shall be understood as the smallest transversal size of the cross section. Currently available technologies for forming openings with the above mentioned diameter range usually require a height to diameter ratio ("aspect ratio") of up to 5. In other words, the thickness of the front platelet in the region surrounding the microchannels needs to be small enough, i.e. in the range of 1 to 50 µm depending on the microchannel diameter. In order to provide sufficient stiffness of the front platelet, reinforcing regions with a substantially higher thickness are provided at locations displaced from the microchannels.

The device of this invention further includes some type of peripheral base element circumferentially arranged around the fluid transmission element. As will be explained in more detail below, the terms "peripheral" and "circumferentially arranged around" refer to their geometric relation towards the fluid transmission element, which is substantially plate shaped. The specific size, shape and material of the peripheral base element are selected in accordance with the application. The device is generally configured to be implantable in a patient, which means that any parts that will be in contact with a patient's body region shall be made of suitable biocompatible materials and have dimensions appropriate for the intended type of implantation. In the present context, a biocompatible material shall be understood as a material that is non-toxic and does not have any other undesirable properties such as allergenicity towards the intended patient.

Advantageous embodiments are defined in the dependent claims and are described below.

In principle it is possible to manage the fluid delivery to and/or fluid withdrawal from the buffer volume by means of a single fluid port. In many situations, however, it is preferable to have two fluid ports, as this will allow establishing a flow-through mode by using one fluid port as the entrance and the other fluid port as the exit. Therefore, according to another embodiment, the fluid interface device has at least two fluid ports (claim 2).

In principle, a fluid port can be arranged in any suitable location of the structure that delimits the buffer volume. According to one embodiment, the fluid port is arranged in the counterplate (claim 3).

According to an embodiment that is particularly advantageous for applications in which the primary face is in contact with blood, e.g. when using the fluid interface as a plasma filtration device, the microchannels have an opening of 0.6 to 2 µm and the primary face is provided with guard elements protruding with respect to a plane defined by microchannel exits in the primary face, the guard elements being formed in such manner as to define at least one transversal limitation over each microchannel exit, the transversal limitation being larger than the microchannel opening and being in the range of 2 to 4 µm (claim 4). The guard elements can be configured as pillars or as substantially parallel ribbons. Although a microchannel diameter of 0.6 to 2 µm is clearly smaller than the size of thrombocytes, the latter may nonetheless be pushed through a microchannel if a substantial pressure gradient is present at the microchannel entrance. Thereby the thrombocyte is deformed and eventually destroyed, but this is highly undesirable and results in debris produced in the buffer volume. By virtue of the guard elements, which define a transverals limitation in at least one direction and thus keep any thrombocytes at a certain distance from the microchannel entrance while allowing a fluid flow in the region adjacent the primary face, the rate of thrombocyte passage through the microchannels is substantially reduced. The height of the guard elements, i.e. their extension protruding from the plane is typically in the range of 1 to 3 µm, particularly about 2 µm.

Advantageously, the front platelet is made of material that is suitable to a photolithographic processing, which is a very convenient technique for forming narrow structures with a well-defined shape. The counterplate should be made of a material that is compatible with that of the front platelet and that has advantageous properties in view of any fluid connections to be attached thereto. Therefore, according to an advantageous embodiment (claim 5), the front platelet is made of silicon (Si) and/or silicon nitride ($Si_3N_4$) and the counterplate is made of glass. Suitable sandwich structures made of Si and $Si_3N_4$ layers are generally known in the field of microtechnology. In some embodiments the front platelet is functionalized, i.e. provided with a suitable coating. The type and thickness of such coating will depend on the particular application. For the sampling of blood plasma there are known functionalizations aiming at the prevention of clot formation and coagulation.

According to an advantageous embodiment (claim 6), the front platelet and the counterplate are joined to each other by anodic bonding. In particular, this method allows formation of strong and medium-tight connections between Si and glass structures.

Various shapes of the fluid transmission element are feasible in principle. In a particularly advantageous embodiment (claim 7), the counterplate is substantially planar and the buffer volume is enclosed within a peripheral protrusion zone of the secondary face of the front platelet. This configuration is favored by the fact that the front plate needs to be processed anyway in order to produce the microchannels; particularly in the case of Si parts there are established methods for forming elevated or recessed regions. As to what concerns the counterplate, which is preferably made of glass, it is generally convenient to use flat or planar shapes.

For many applications it is advantageous if the buffer volume comprises at least two separate compartments, each one being in connection with a respective microchannels array and each being provided with at least one fluid port (claim 8). This embodiment effectively incorporates two or possibly more than two independently operable subunits of the fluid interface, whereby it is possible to use each subunit for a separate task. In particular, one could use one subunit for sampling purposes, i.e. for withdrawing an amount of fluid such as blood plasma or cerebrospinal fluid from the patient, whereas another subunit could be used for delivery purposes, i.e. for introducing a therapeutic or prophylactic agent to the patient. However, it should be understood that both subunits will generally need to allow for withdrawal and for delivery of fluids in order to perform subsidiary tasks such as flushing.

According to an advantageous embodiment, the fluid interface device further comprises a spacer element with a first spacer face that is adhesively connected to an external face of the counterplate, the spacer element comprising traversing channels connecting the first spacer face and a second spacer face, each traversing channel being arranged to form a passage between one of the counterplate's fluid ports and a corresponding channel opening at the second spacer face (claim 9). Such a spacer element opens various possibilities for establishing a connection between the fluid transmission element, which is located very close to a body region and will generally be small and sensitive, and an external unit used to drive and supply the device. Although the spacer element could be made of a variety of compatible materials, it is advantageously made of a thermoplastic polymer, particularly a non-fluorinated thermoplastic polymer that is suitable for connection by means of an adhesive.

Advantageously, the fluid interface device further comprises a fluid supply connector and means for releasably attaching the fluid supply connector to the spacer element, the fluid supply connector comprising connector channels each leading from a lateral entrance port to an exit port coinciding with a channel opening at the second spacer face when the fluid supply connector is attached to the spacer element (claim 10). Such an embodiment is particularly useful for a device intended for implantation in a patient's blood vessel wall. Firstly, such a configuration allows carrying out the implantation of the comparatively compact device without being hindered by any supply tubing connecting the device with an extracorporeal unit, as the latter can be connected after implantation. Secondly, in case of an infection in the supply tubing system, e.g. in a region where such tubing is conducted through the skin, it would be possible to continue using the implanted fluid interface device and merely install a new supply system.

For construction purposes it is advantageous if each one of the connector channels is formed as a pair of grooves in adjacent faces of mutually contacted connector parts (claim 11). Such a design allows comparatively simple production of curved or bent channels in a solid piece.

According to an advantageous embodiment, the fluid transmission element and the base element are sealingly connected to each other by a ridge structure surrounding the fluid transmission element, the ridge structure being made of a biocompatible thermoplastic formed around the fluid transmission element by injection molding (claim 12). In the present context, a biocompatible material shall be understood as a material that is non-toxic and does not have any other undesirable properties such as allergenicity towards the intended patient.

In a first, inner contacting region of the ridge structure a medium tight closure is formed against an outer circumferential surface of the fluid transmission element as a result of the injection molding process. For this purpose, it is advantageous if the fluid transmission element is provided with a structured peripheral region. In particular, the front platelet may be formed with a radially protruding section provided with holes, rims or undercuts which will be filled up with injected thermoplast and thereby will strongly improve the connection between the ridge structure and the fluid transmission element.

In a second, outer contacting region of the ridge structure, a medium tight connection is formed with the peripheral base element by means of a suitable contacting method. The best choice of such contacting method will depend on the materials to be joined. According to an advantageous embodiment, the peripheral base element is sealingly connected to the ridge structure by injection molding thereon a covering part; according to another advantageous embodiment, the peripheral base element is sealingly connected to the ridge structure by ultrasonic welding (claim 13). As will be known to the skilled person, the use of a welding technique requires that the parts to be joined are made of compatible materials, preferably of the same material, which in the present case means a compatible or identical biocompatible thermoplastic polymer.

An important application of the fluid interface device is for implantation in a patient's blood vessel wall, particularly in a venous wall. Advantageously, the device is implanted in a wall section of a patient's upper arm vein. Therefore, according to an advantageous embodiment (claim 14) the peripheral base element is formed as a foamed pad of a thermoplastic fluoropolymer which is suitable for implantation in a patient's blood vessel wall, and the injection molded ridge structure is formed as a non-foamed body of said thermoplastic fluoropolymer. The implantation of various types of pads into venous walls has been extensively studied and thus is basically known. Accordingly, there exist well tested materials for this purpose, among which foamed thermoplastic fluoropolymers have turned out to be very suitable. In order to connect the foamed pad to the ridge structure, which is preferably done by ultrasonic welding, it is advantageous if the injection molded ridge structure is made of the same thermoplastic fluoropolymer as the foamy peripheral pad. By the above definitions, both parts are made of biocompatible materials. Implanting the fluid interface device in a patient's venous wall is a promising approach for establishing a reliable, uninterrupted sampling of the patient's venous blood and for regulated delivery of any suitable therapeutic or prophylactic agent. An important application field is for diabetic patients.

Another application field of the fluid interface requires fixation to an osseous structure of the patient, e.g. to a skull section. Therefore, according to another advantageous embodiment (claim 15) the peripheral base element is formed as rigid frame structure suitable for fixation to an osseous structure of a patient. Appropriate fixation means are known, e.g. for implantation of hearing aids. In the present context, the fluid interface device could be applied to a patient's skull for sampling intracranial fluid and/or for delivering thereto any suitable therapeutic or prophylactic agent thereby allowing to avoid the blood-brain-barrier. For this mode of use the microchannels of the device will serve to prevent leucocytes and antibodies of the intracranial fluid from clogging the microchannel array and/or entering into the buffer volume.

A further application field of the fluid interface relates to subcutaneous or possibly intramuscular placement which does not require firm fixation to a body part. Accordingly, in a further embodiment (claim 16) the fluid interface device further comprises a fluid supply connector attached to the spacer element, the fluid supply connector comprising connector channels each leading from an entrance port to an exit port coinciding with a channel opening at the second spacer face, the fluid supply connector being formed as a sealing mass that encapsulates the spacer element and the fluid transmission element and that furthermore forms the peripheral base element. In such embodiments a certain degree of fixation will be provided by a transcutaneous passage connecting the fluid interface device to an external control and supply device.

According to an advantageous embodiment (claim 17), the fluid interface device is configured as an elongated body having a proximal end, a distal end and a lateral surface therebetween, the front platelet of the fluid transmission element being disposed to form part of the lateral surface.

Advantageously, the distal end of the elongated body has a pointed shape (claim 18), which is generally helpful for inserting the distal end into a body cavity or into a blood vessel. In most cases the pointed shape will not be sharp like e.g. a punction needle, so it will not be used to punch through a patient's tissue. Rather than that, the pointed end serves as a guidance for insertion into a pre-existing passage. Advantageously, the outer diameter of the elongated body does not exceed a value of a few millimeters. Preferably, the outer diameter does not exceed a value of 8 mm, more preferably 6 mm and even more preferably 4 mm.

According to a particularly advantageous embodiment, the elongated body is provided with a longitudinal passage extending from the distal end to the proximal end (claim 19). Such a longitudinal passage serves to receive a guide wire as generally known in the field of catheter based interventions. With such a configuration it is possible to move the fluid interface device along a suitably placed guide wire in a sliding manner. For example, in order to insert the fluid interface device into a patient's vein, a guide wire is first driven into the patient's body at a convenient transdermal entry point and then advanced until reaching a predetermined venous entry point. The guide wire is then driven further so as to punch into the venous wall. Thereafter, the fluid interface is slidingly driven into the body along a path defined by the guide wire. By having a fluid interface device with a pointed distal end the insertion into the venous wall previously punctured by the guide wire is substantially facilitated.

According to a further advantageous embodiment, the peripheral base element forms an outer sheath of the elongated body (claim 20). This allows fabricating the device by first assembling the various inner components forming the elongated body including the fluid transmission element and subsequently applying the outer sheath around the assembly. It is also advantageous it the peripheral base element including the sheath is made of a biocompatible thermoplastic.

Advantageously, the front platelet is made of material that is suitable to a photolithographic processing, which is a very convenient technique for forming narrow structures with a well-defined shape. The counterplate should be made of a material that is compatible with that of the front platelet and that has advantageous properties in view of any fluid connections to be attached thereto. Therefore, according to an advantageous embodiment (claim 21), the front platelet and the counterplate are made of silicon (Si) and/or silicon nitride ($Si_3N_4$). Suitable sandwich structures made of Si and $Si_3N_4$ layers are generally known in the field of microtechnology. In some embodiments the front platelet is functionalized, i.e. provided with a suitable coating. The type and thickness of such coating will depend on the particular application. For the sampling of blood plasma there are known functionalizations aiming at the prevention of clot formation and coagulation.

Advantageously, the one or several fluid ports are configured as openings in the counterplate.

According to one embodiment, the buffer volume comprises a single compartment being in connection with a respective microchannels array and one fluid port (claim 22). Such an embodiment allows for a particularly compact construction with small external diameter, which may be as small as about 3 mm. It may be used, for example, for continuous or periodic withdrawal of plasma from a patient. This is particularly advantages for conducting a photometric glucose determination undisturbed by blood cells.

As already mentioned, it is possible to manage the fluid delivery to and/or fluid withdrawal from the buffer volume, or from each subunit if applicable, by means of a single fluid port. In many situations, however, it is preferable to have two fluid ports per buffer volume or subunit, as this will allow establishing a flow-through mode by using one fluid port as the entrance and the other fluid port as the exit. Therefore, according to another embodiment, the buffer volume comprises a single compartment being in connection with a respective microchannels array and two fluid ports (claim 23).

According to a further embodiment, the buffer volume comprises two separate compartments, each compartment being in connection with a respective microchannels array and one fluid port (claim 24). This embodiment effectively incorporates two independently operable subunits of the fluid interface, whereby it is possible to use each subunit for a separate task. In particular, one could use one subunit for sampling purposes, i.e. for withdrawing an amount of fluid such as blood plasma or cerebrospinal fluid from the patient, whereas another subunit could be used for delivery purposes, i.e. for introducing a therapeutic or prophylactic agent to the patient. However, it should be understood that both subunits will generally need to allow for withdrawal and for delivery of fluids in order to perform subsidiary tasks such as flushing. Therefore, according to still another embodiment the buffer volume comprises two separate compartments, each compartment being in connection with a respective microchannels array and two fluid ports (claim 25).

In one embodiment with two separate compartments, these are arranged at substantially opposite sides of the elongated body. This allows for a comparatively short overall construction. However, for certain applications it is desirable to have both compartments at the same side of the elongated body, i.e. one compartment is closer to the distal end and the other compartment is closer to the proximal end (claim 26). This is particularly advantageous e.g. for intravenous applications in which one side of the device may be pushed against the venous wall and will thus have poor fluid communication with the venous blood in the lumen. Clearly, however, it may be necessary to rotate the device about its longitudinal axis if for some reason it has assumed an undesirable orientation with the fluid transmission element in direct contact with the venous wall.

Advantageously, the elongated body comprises for each fluid port a fluid passage leading to a channel opening at the proximal end of the elongated body (claim 27). This allows for a geometrically favorable co-axial fluid access without any undesirable laterally protruding parts.

According to an advantageous embodiment, the proximal end is provided with means for attaching a fluid supply connector to each one of the corresponding channel openings (claim 28). This allows for convenient pre-assembly of an operational unit comprising a fluid interface device and a fluid supply line, which can consist of several coaxial tubings. It will be understood that such a pre-assembly and subsequent application of a thermoplastic sheath will require suitable holding means.

The above defined fluid interface device and its various embodiments can be used for a variety of applications. By virtue of its elongated body and compact lateral dimensions, the fluid interface device can be inserted into a blood vessel, preferably a well-perfused vein. Alternatively, it can be inserted into a patient's brain, or simply in a subcutaneous region. In such embodiments a certain degree of fixation will be provided by a transcutaneous passage connecting the fluid interface device to an external control and supply device.

According to a further embodiment, the peripheral base element is configured as a wall section of a tubular segment suitable for containing a patient's body fluid region (claim 29). An important application field is for diabetic patients.

The peripheral base element is configured as a wall section of a tubular segment, the latter being suitable for containing a patients body fluid. For many applications the tubular segment is configured to form part of a grafted arteriovenous shunt when the device is implanted in a patient. Accordingly, the patient's body fluid region that is in contact with the primary face of the fluid transmission element is a region within the tubular segment. In case of a grafted arteriovenous shunt, the body fluid is the patient's blood streaming through the shunt.

According to a further advantageous embodiment, the peripheral base element is integrally formed on the tubular segment which is also made of the biocompatible thermoplastic (claim 30). In other words, the tubular segment and the peripheral base element connected thereto and, advantageously also the ridge structure, are all formed as one piece of the same thermoplastic material.

An important application of the fluid interface device is for implantation within a grafted arteriovenous shunt of a patient. Possible graft locations and configurations are straight forearm (radial artery to cephalic vein), looped forearm (brachial artery to cephalic vein) and straight upper arm (brachial artery to basilica or axillary vein). Further possibilities are thigh grafts, necklace grafts (axillary artery to axillary vein), and axillary-atrial grafts. Therefore, according to an advantageous embodiment the tubular segment is provided at both ends thereof with means for connecting to a patient's systemic circuit (claim 31). Preferably, these are releasable connecting means. This embodiment will allow connecting the device's tubular segment, which is typically made of a biocompatible thermoplastic with advantageous formability properties, onto a counterpart consisting of the synthetic graft tubing connected to the patient's artery or vein. Such graft tubings are typically made of polytetrafluoroethylene (PTFE), which would not be suitable as a material for forming the ridge structure adjacent to the fluid transmission element.

According to another aspect of the invention (claim 32), there is provided a system for delivering fluid to and/or withdrawing fluid from a patient's body region. The system comprises a fluid interface device as defined above and furthermore comprises fluid storage means and fluid transfer means for controlled fluid delivery to and fluid withdrawal from the buffer volume via the fluid ports. The system is configured to be able to perform at least the following steps according to a pre-defined step sequence:
  a) running flushing medium through the buffer volume;
  b) running flushing medium through the microchannels array;
  c) withdrawing patient's body fluid through the microchannels array; and
  d) delivering a therapeutic agent to the patient.

According to an advantageous embodiment of the system, the fluid transfer means are configured as transdermal tubing (claim 33). Such devices are generally known e.g. as Hickman or Broviac catheters and comprise a tubing section that passes through a patient's skin at an appropriate location. Advantageously, the tubing has a cuff to be placed at the passage through the skin serving as a mechanical fixation and as an antimicrobial barrier. By using a porous cuff, e.g. made of PTFE, cellular ingrowth sets in after placement of the cuff; to reduce the risk of infections, it is furthermore known to incorporate antimicrobial agents such as silver.

According to another advantageous embodiment, the fluid transfer means comprise:
  a subcutaneously implantable injection port having at least one injection chamber, each injection chamber having an upper inlet opening covered by a pierceable septum and an exit opening;
  at least one two-ended fluid transfer line connectable at one end thereof to said exit opening and connectable at the other end thereof to a corresponding fluid port of said fluid interface device.

Such devices are generally known, e.g. as "port-a-cath" systems.

In many applications it would be desirable to deliver a therapeutic agent to a patient more or less continuously, optionally adapting the momentary delivery rate to a momentary therapeutic need. The latter could be determined continuously or intermittently by a suitable monitoring method. One example is continuous delivery of insulin in accordance with a momentary blood glucose level ("on-demand-delivery"). In order to implement such a delivery scheme, it is advantageous to adopt an embodiment of the system which further comprises means for establishing a continuous or intermittent flow of supply medium through the buffer volume, whereby a fraction of supply medium is delivered to the patient through the fluid transmission element (claim 35). As will be understood, the "supply medium" will generally be a liquid medium containing the required therapeutic agent in a suitable concentration. The supply medium is generally driven into the buffer volume through a first fluid port thereof.

In one embodiment, the system is configured to be operated in such manner that a major fraction of the supply medium will flow out of the buffer volume through a second fluid port, with the remainder being driven through the fluid transmission element and thereby delivered to the patient. As will also be understood, the delivered fraction depends on the relative conductance of the fluid transmission element as compared to the conductance of the fluid exit system comprising the second fluid port. In certain applications, the delivered fraction will be in the range of 1 to 20%, particularly about 5 to 15%, and more particularly about 10%. Typically, a pressure difference of 10 to 30 mbar will be established across the fluid transmission element, i.e. the pressure will be higher by such an amount in the buffer volume versus the patient's body region.

In another embodiment, the system is configured to be operated in a semi-continuous, portionwise manner, e.g. by means of basically known controlled fluid piston means which rely on the incompressible nature of liquid media. This allows one to introduce and/or to withdraw well defined volume portions of e.g. 1 to 10 µl to and/or from the patient's body. In this manner one can implement a variety of dosage and/or dilution regimes by selecting appropriate sequences of fluid input and withdrawal.

According to a further aspect of the invention (claim 36), there is provided a method of operating the system defined above, in which method a flushing medium is delivered to the buffer volume so as to maintain an overpressure relative to a base pressure in the patient's body region when the system is not withdrawing patient's body fluid or delivering a therapeutic agent to the patient, thereby preventing any flow from the patient's body region through the microchannels into the buffer volume.

The flushing medium typically will be a 30%/70% ethanol/water solution containing a known anticoagulant such as heparin or aspirin. By diffusing from the buffer medium through the microchannels, the anticoagulant will contribute to avoid undesirable blood clot formation in or near the microchannel array.

In principle one could establish a small but constant flow of flushing medium from the buffer volume into the patient's body region. However, this would require excessive amounts of flushing medium and is generally not desirable. In many practical situations it will be sufficient to simply keep the buffer volume under a small overpressure relative to a base pressure in the patient's body region. To do so, one can periodically feed a small portion of buffer medium into the buffer volume, for example 10 µl every 5 min.

The above defined system and operating method may be termed "liquid membrane management" in the sense that an undesirable clogging of the microchannels, but also an undesirable entry of certain cells and other particles into the buffer volume is avoided by maintaining a layer of protecting liquid in the microchannels at all times.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein:

FIG. 8 shows the front platelet of FIG. 4 with a counterplate attached thereto, in a plan view seen from the secondary face;

FIG. 9 shows the front platelet and counterplate of FIG. 8 in a sectional view according to section B-B;

FIG. 10 shows the front platelet and counterplate of FIG. 8 in a sectional view according to section A-A;

FIG. 11 shows the front platelet and counterplate of FIG. 8 in a perspective view;

DETAILED DESCRIPTION OF THE INVENTION

Figure 1:
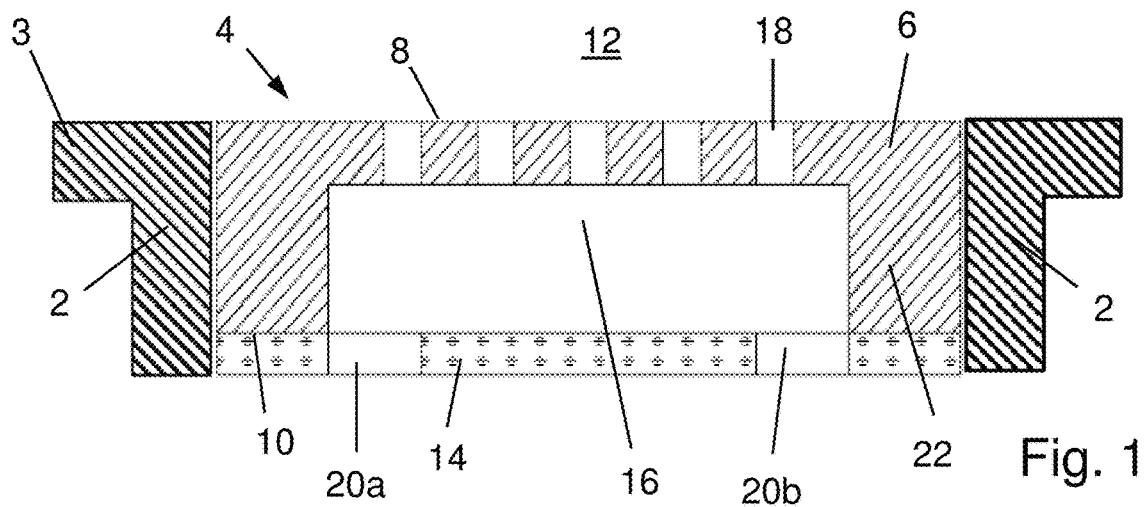
FIG. 1 shows a first embodiment of a fluid interface device, in a sectional view.
Figure 2:
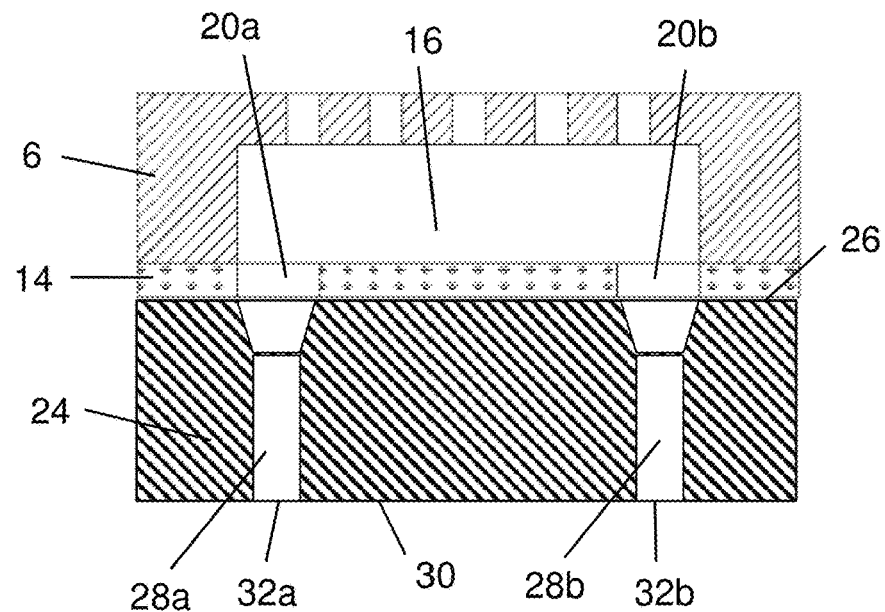
FIG. 2 shows a part of the fluid interface device of FIG. 1 with an attached spacer element, in a sectional view.

In order to better explain the general principle of the present invention, FIGS. 1 and 2 show a basic embodiment of a fluid interface device, in a schematic representation and not to scale. The device comprises a peripheral base element 2, which in the example shown is configured as a simple surrounding piece with an outwardly protruding flange 3. A composite part generally denoted as fluid transmission element 4 is sealingly connected to the base element 2 and forms a central portion of the device. The base element 2 is generally intended to provide some kind of attachment or fixture to a patient's body part and could be integrally formed with the fluid transmission element. The latter comprises a front platelet 6 with a primary face 8 and with a secondary face 10 opposed thereto. The primary face is in contact with a patient's body fluid region generally denoted as 12 when the device is implanted in the patient. The fluid transmission element further comprises a counterplate 14 that is sealingly stacked against the secondary face of the front platelet and forms a buffer volume 16 therebetween. Importantly, the front platelet 6 comprises at least one array of microchannels 18 defining a fluid passage between the buffer volume and the primary face. Depending on the intended use of the device, the microchannels are formed with an opening of 0.2 to 10 μm. The counterplate has two fluid ports 20a; 20b for fluid delivery to and/or fluid withdrawal from the buffer volume.

In the example shown, the counterplate 10 is substantially planar and is made of glass. In contrast, the front platelet 6 has a peripheral protrusion zone 22 directed towards the counterplate 10 and forming a lateral wall enclosing the buffer volume 16. The front platelet 6 is made of Si and/or Si$_3$N$_4$ and is joined to the counterplate 14 by anodic bonding.

FIG. 2. shows the fluid interface device of FIG. 1, but without peripheral base element 2. A spacer element 24 made of a thermoplastic polymer has a first spacer face 26 that is connected to an external face of the counterplate 14 by means of a suitable adhesive. The spacer element 24 comprises traversing channels 28a; 28b connecting the first spacer face and a second spacer face 30 opposed therefrom. Each traversing channel is arranged to form a passage between one of the counterplate's fluid ports 20a, 20b and a corresponding channel opening 32a 32b at the second spacer face. As will be seen from forthcoming examples, the spacer element 24 is a useful means for coupling with an appropriately configured tubing connector for supply and delivery of fluid from and to an external device.

Figure 3:
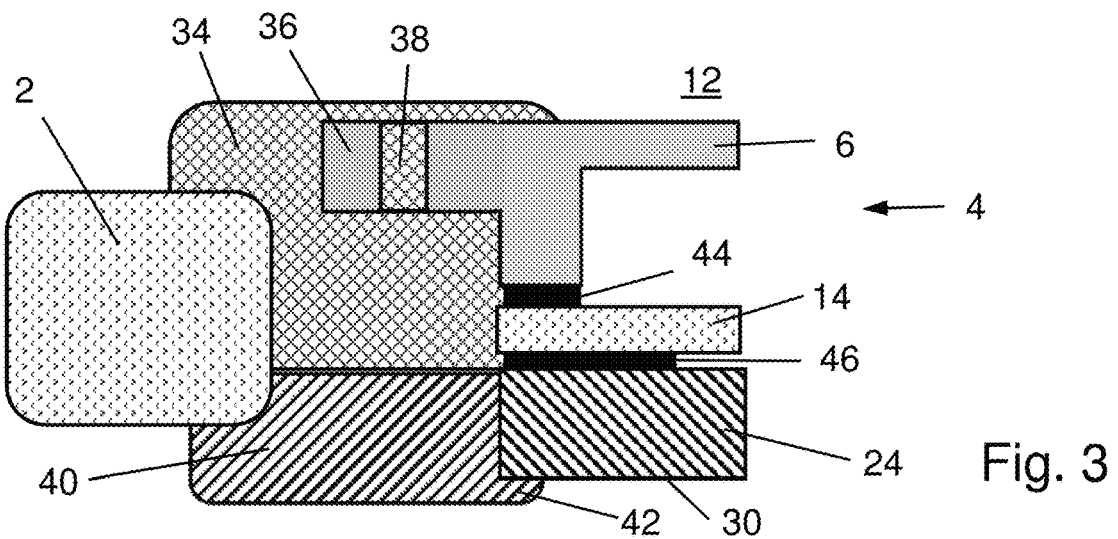
FIG. 3 shows a second embodiment of a fluid interface device, in a schematic sectional view.
Figure 4:
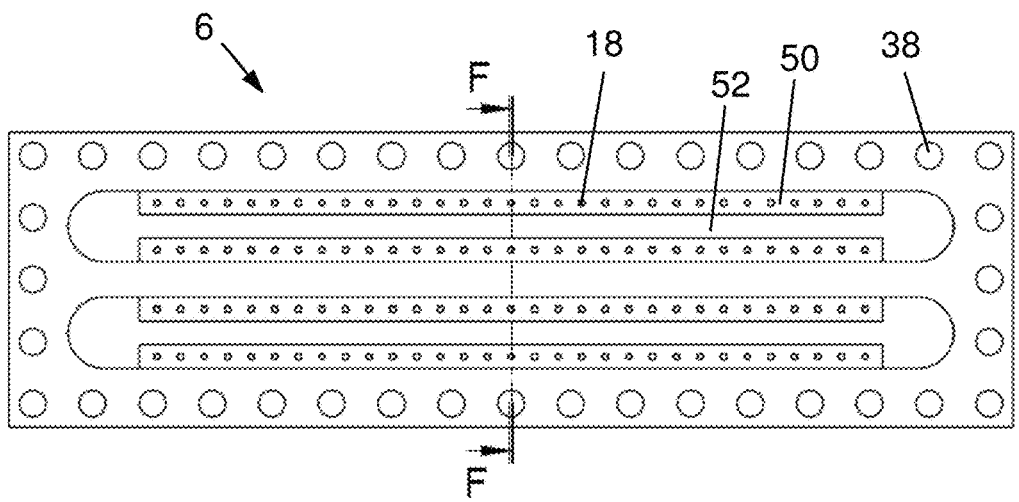
FIG. 4 shows a front platelet of a third embodiment, in a plan view seen from the secondary face.
Figure 5:
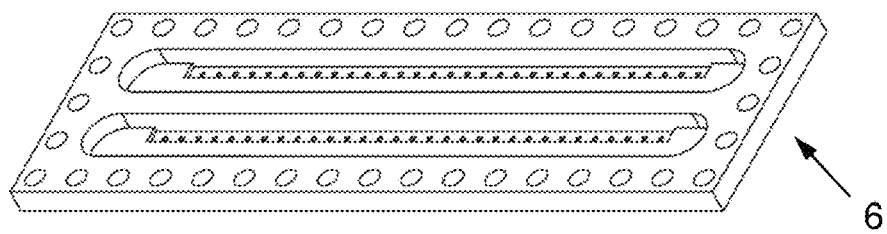
FIG. 5 shows the front platelet of FIG. 4 in a perspective view.
Figure 6:
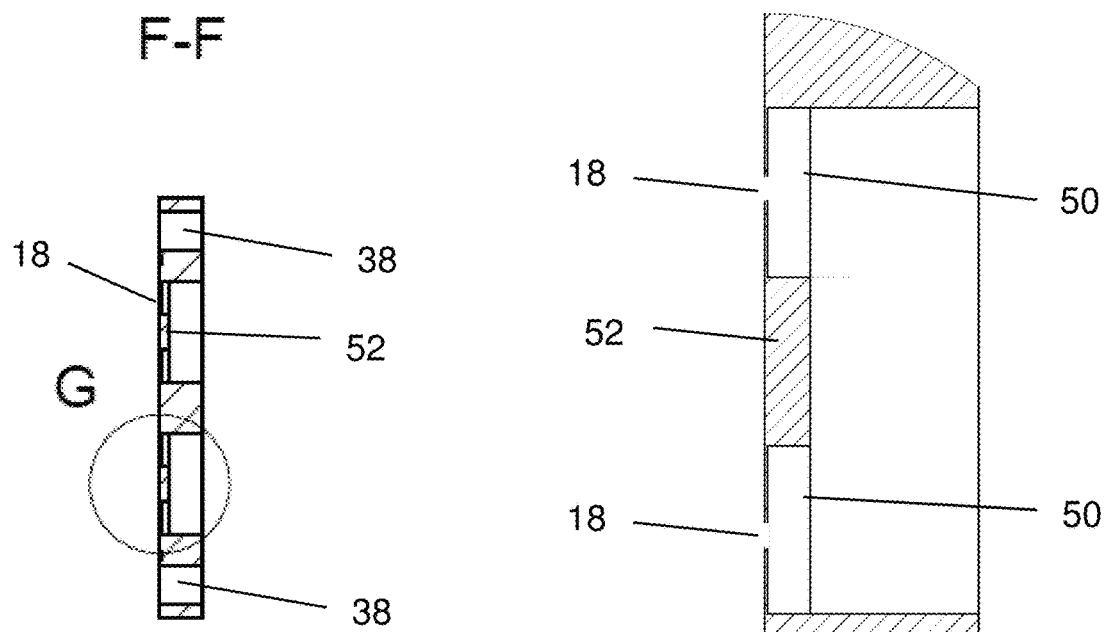
FIG. 6 shows the front platelet of FIG. 4 in a sectional view according to section F-F.
Figure 7:
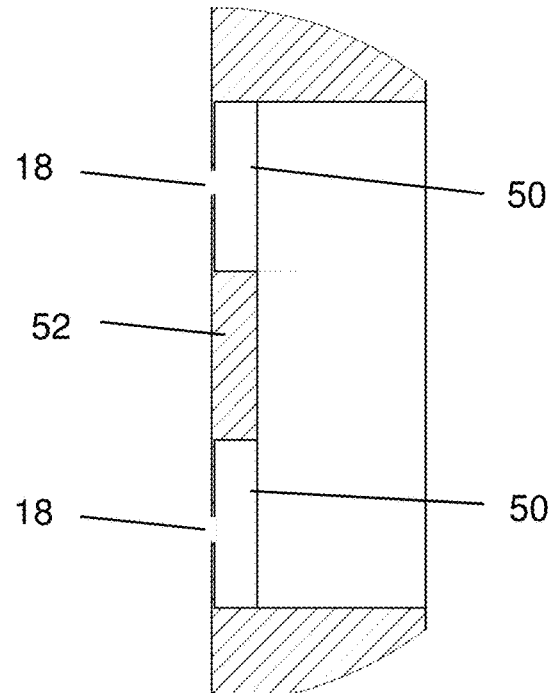
FIG. 7 shows an enlarged portion G of FIG. 6.
Figure 12:
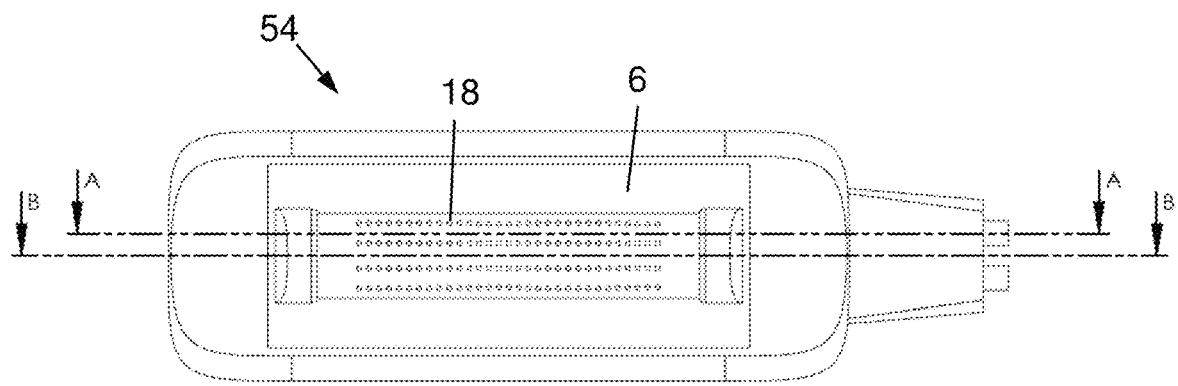
FIG. 12 shows a fluid interface device including the front platelet and counterplate of FIG. 8 and a fluid supply connector attached thereto, in a plan view seen from the primary face.

The basic structure of a fluid interface device suitable for implantation in a venous wall is further illustrated in FIG. 3. For this purpose the peripheral base element 2 is formed as a foamy pad of a thermoplastic fluoropolymer which is suitable for implantation in a patient's blood vessel wall. Such a materials are commercially available, e.g. as GORE® ACUSEAL Cardiovascular Patch. In order to form a compact, reliable and medium tight connection between the foamy pad 2 and the fluid interface structure 4, an arrangement as shown in FIG. 3 can be used. Such arrangement comprises a ridge structure 34 surrounding the fluid transmission element 4 and sealingly connecting the latter with the base element 2. The ridge structure 34 is made of a biocompatible thermoplastic fluoropolymer formed around the fluid transmission element 4 by injection molding. In order to promote a good adhesion of the ridge structure 34 with the fluid transmission element 4, the front platelet 6 has an outwardly protruding collar 36 provided with a plurality of holes 38. As shown in FIG. 3, the injection molded material of the ridge structure 34 is disposed around the collar 36 and within the holes 38, which provides a form-locking effect. It will be understood that instead of holes the collar could be provided with other types of locking structures such as recesses and protrusions.

In the example shown in FIG. 3, a covering part 40, which is generally ring-like and made of the same thermoplastic fluoropolymer as the ridge structure 34 surrounds the spacer element 24 and is in contact with the ridge structure 34. The ridge structure 34 and the covering part 40 surround a portion of the peripheral base element 2 in a C-type manner. The C-shaped boundary zone between the peripheral base element 2, the ridge structure 34 and the covering part 40 is connected by ultrasonic welding. It will be understood that this convenient joining method requires that the thermoplastic fluoropolymer of the ridge structure and of the covering part is either the same as or is compatible with the fluoropolymer forming the foamy pad peripheral base element 2. In the example shown, the covering part 40 is formed with an overlap zone 42 extending over the second face 30 of the spacer element 24.

As also shown in the schematic representation of FIG. 3, the front platelet 6 and the counterplate 14 are joined to each other in a first contacting zone 44 formed by anodic bonding.

Further, the counterplate 14 and the spacer 24 are joined to each other in a second contacting zone 46 by means of a suitable adhesive.

A convenient manner of assembling the exemplary device of FIG. 3 may be summarized as follows:
- place a previously assembled fluid transmission element 4 onto a corresponding holder with the front platelet 6 downwards
- form the peripheral ridge 34 by injection molding around the fluid transmission element 4
- stack the spacer element 24 onto the counterplate 14 and join with suitable adhesive
- place a suitably formed peripheral base element 2 made of foamy thermoplastic fluoropolymer on top of the peripheral ridge 34
- separately form the cover part 40 and stack the same on top of the peripheral ridge 34 and spacer element 24
- connect the cover part 40, the peripheral ridge 34 and the peripheral base element 2 sandwiched therebetween by means of ultrasonic welding.

Further details of an embodiment of the fluid interface device suitable for implantation in a blood vessel are illustrated in FIGS. 4 to 18. Features corresponding to those in the embodiments explained above are generally denoted with the same reference numerals as above.

As will be seen from FIGS. 4 to 7, the microchannels 18 are positioned in elongated grooves 50 formed in the front platelet 6. The grooves 50 constitute a part of the front platelet having minimal thickness so as to allow formation of the narrow microchannels 18. Also shown in FIGS. 4 to 7 are the holes 38 formed in the collar zone 36. A thicker platelet zone 52 located between a pair of grooves 50 serves as mechanical reinforcement.

As evident from FIGS. 8 to 11, a counterplate 14 stacked on the secondary side of the front platelet 6 leaves free the collar zone 36. In the example shown there are two separate buffer volumes 16a and 16b, each of which is provided with a pair of fluid ports 20a, 20b or 20c, 20d, respectively.

Figure 13:
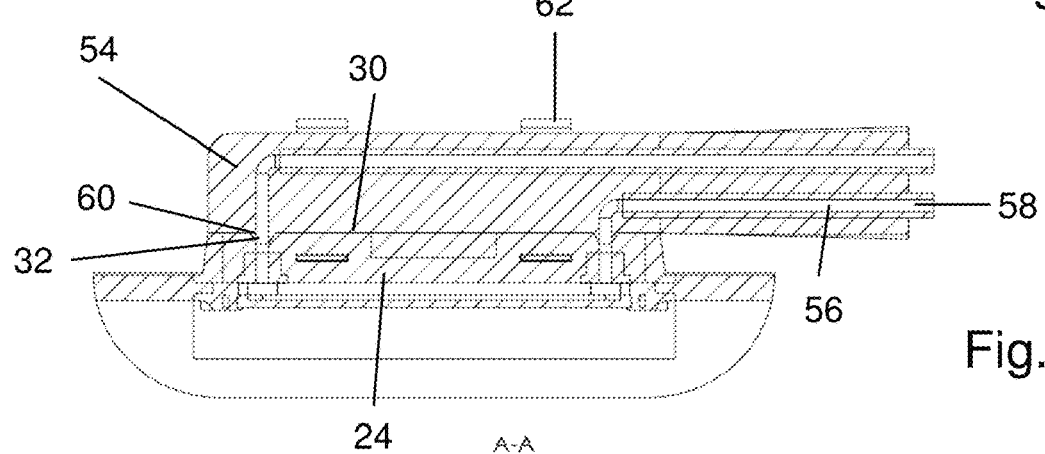
FIG. 13 shows the arrangement of FIG. 12 in a sectional view according to section A-A.
Figure 14:
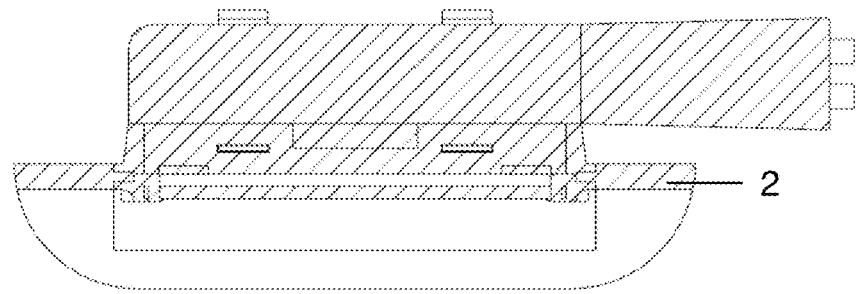
FIG. 14 shows the arrangement of FIG. 12 in a sectional view according to section B-B.
Figure 15:
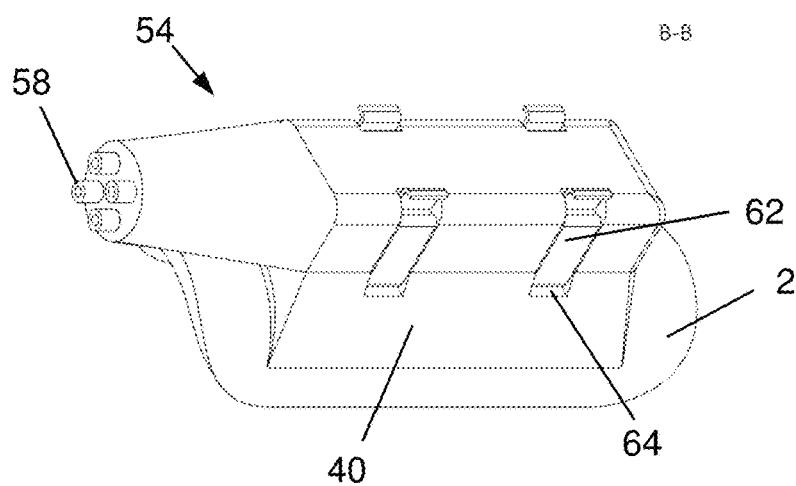
FIG. 15 shows the arrangement of FIG. 12 in a perspective view.
Figure 16:
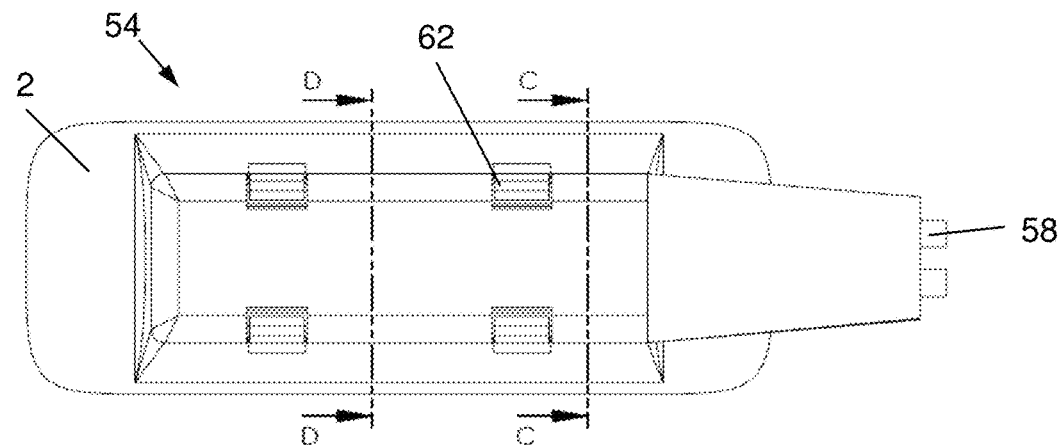
FIG. 16 shows the arrangement of FIG. 12 in a plan view seen from the secondary face.
Figure 17:
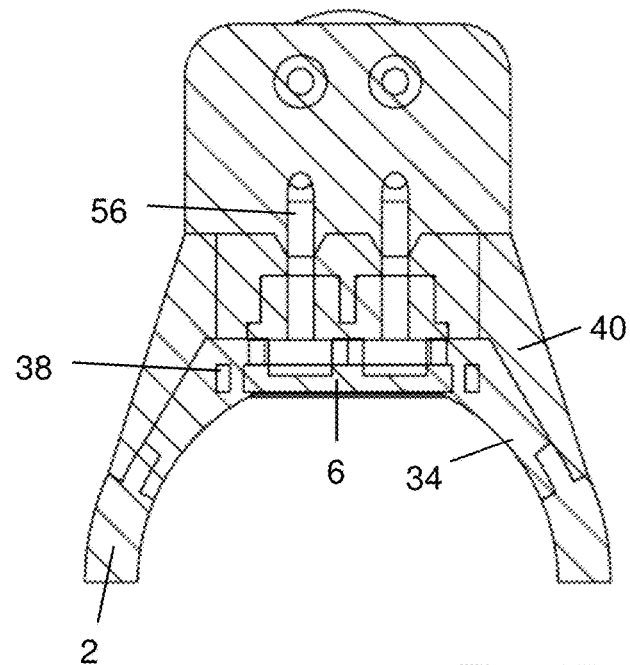
FIG. 17 shows the arrangement of FIG. 16 in a sectional view according to section C-C.
Figure 18:
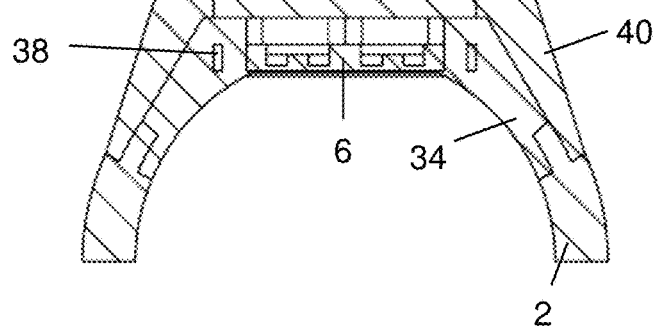
FIG. 18 shows the arrangement of FIG. 16 in a sectional view according to section D-D.
Figure 19:
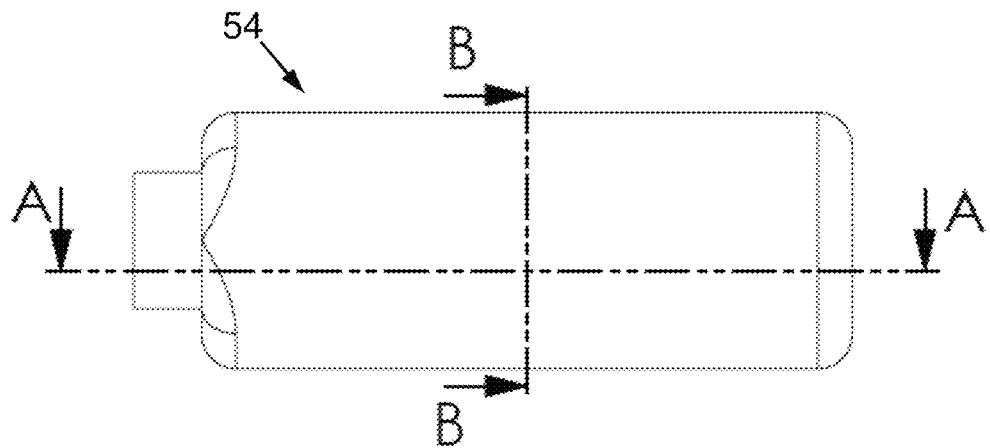
FIG. 19 shows another fluid interface device including the front platelet and counterplate of FIG. 8 and a fluid supply connector attached thereto, in a plan view seen from the side opposite to the primary face.
Figure 20:
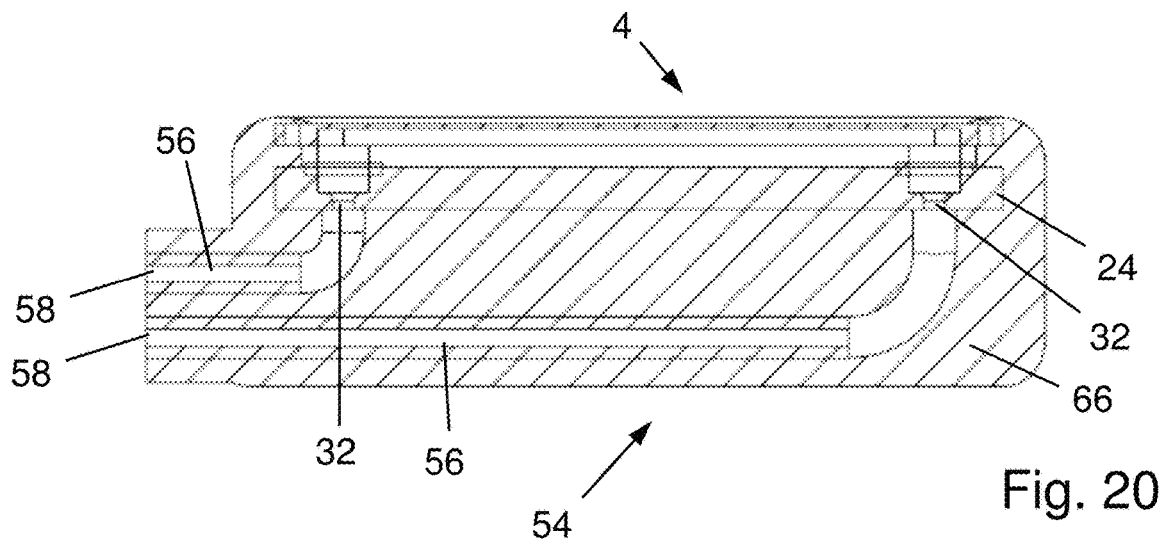
FIG. 20 shows the arrangement of FIG. 19 in a sectional view according to section A-A.
Figure 21:
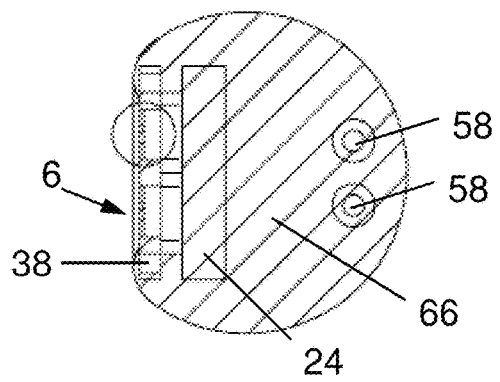
FIG. 21 shows the arrangement of FIG. 19 in a sectional view according to section B-B.
Figure 22:
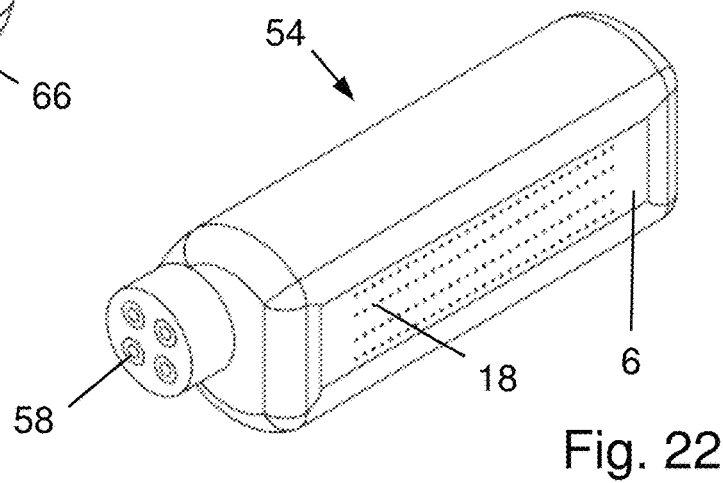
FIG. 22 shows the arrangement of FIG. 19 in a perspective view.

FIGS. 12 to 18 show a fluid interface with a fluid supply connector 54 attached thereto. In particular, FIG. 13 shows connector channels 56 each leading from a lateral entrance port 58 to an exit port 60 coinciding with a channel opening 32 at the second spacer face 30. As shown in FIGS. 15, 16 and 18, the arrangement has four hook-like elements 62 for releasably attaching the fluid supply connector 54 to the spacer element 24. In the example shown, the hook-like elements 62 traverse suitable openings 64 provided in the covering part 40 placed on top and around spacer 24. The arrangement shown in these figures comprises two separate compartments each comprising a buffer volume, a fluid transmission element and two fluid ports.

As illustrated in FIGS. 17 and 18, the ridge structure 34 and the peripheral base element 2 are formed having a concave cross section dimensioned in accordance with the cross section of a blood vessel into which the entire device can be implanted.

FIG. 18 furthermore shows an advantageous manner of sealingly connecting the peripheral base element 2 and the ridge structure 34 by injection molding thereon thereon the covering part 40, whereby a medium-tight closure is formed between parts 40 and 34 and also with part 2 inserted therebetween.

A further embodiment suitable for subcutaneous or intramuscular placement is shown in FIGS. 19 to 22. A fluid transmission element generally denoted as 4 is provided with a spacer element 24 in the manner as described further above. Connector channels 56 are provided to form a fluid connection between entrance ports 58 and corresponding spacer channel openings 32. The fluid supply connector (54) is configured as a sealing mass which forms an encapsulation of the spacer element 24 and at the same time forms the peripheral base element 2.

Figure 23:
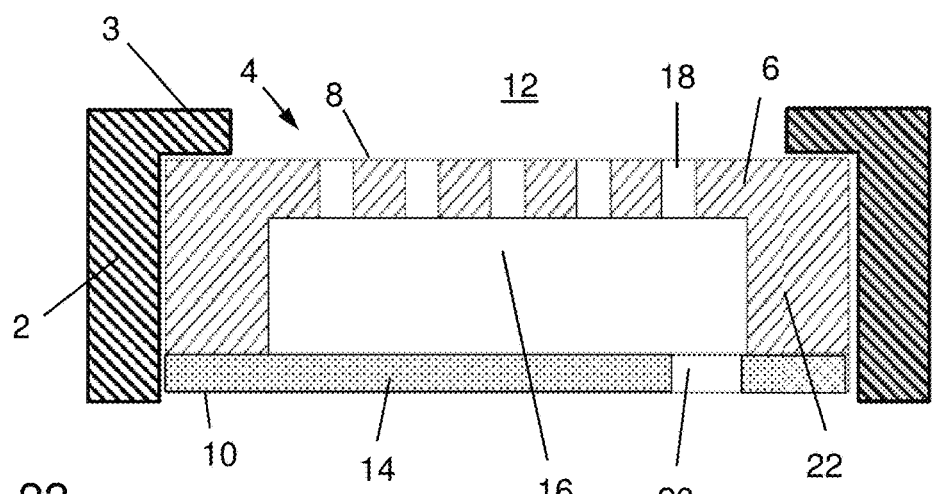
FIG. 23 shows a basic part of a further fluid interface device, in a sectional view.
Figure 24:
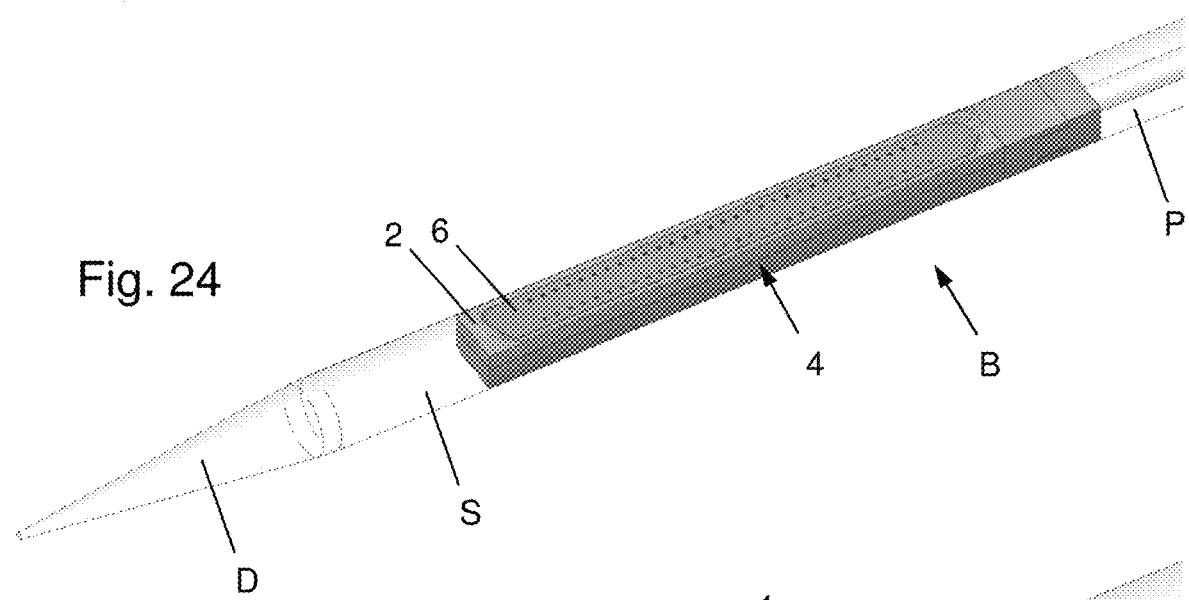
FIG. 24 shows a fourth embodiment of a fluid interface, in a schematic perspective view.
Figure 25:
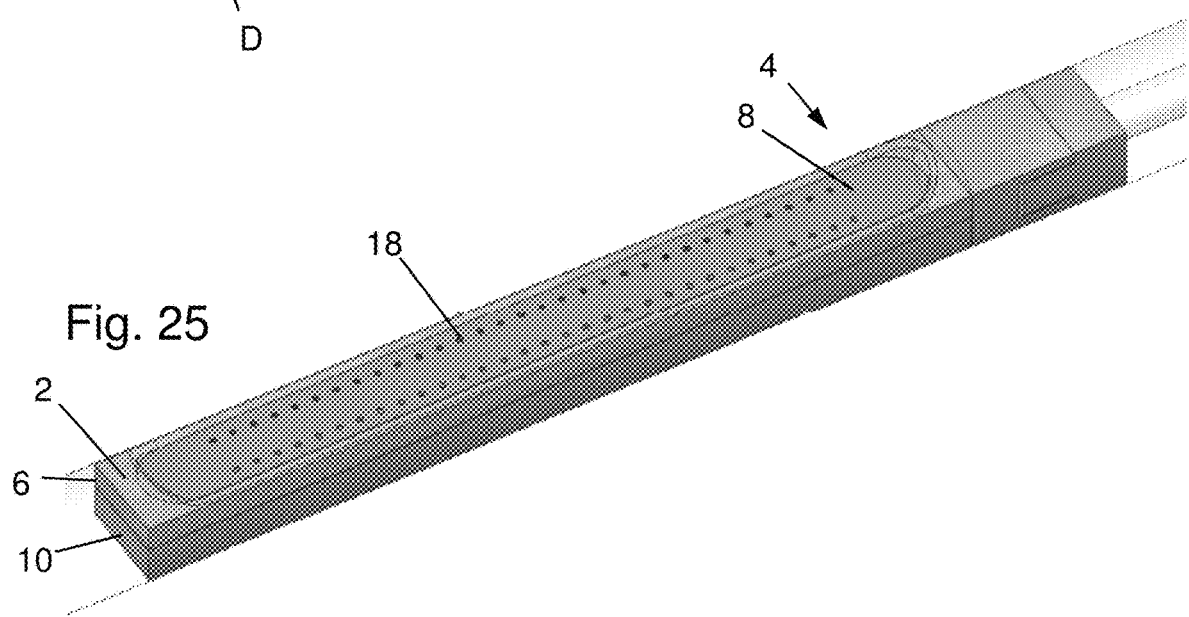
FIG. 25 shows an enlarged view of a detail of FIG. 24.
Figure 26:
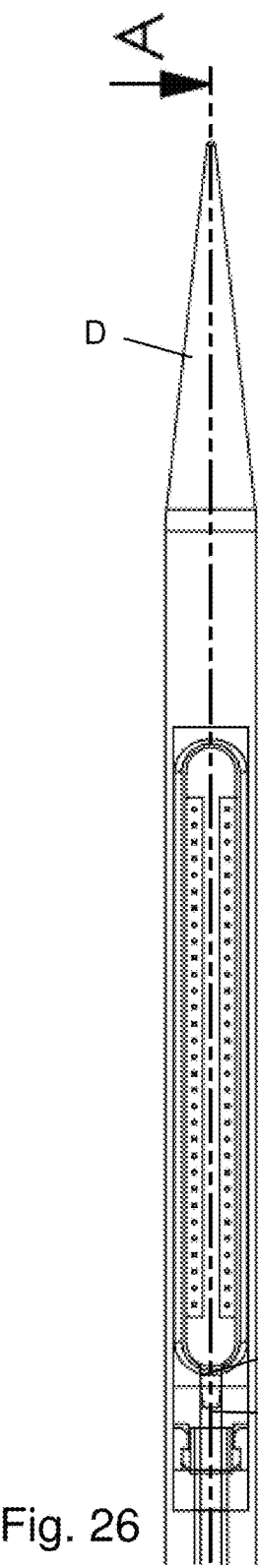
FIG. 26 shows the fluid interface device of FIG. 24 in a plan view seen from the secondary face.
Figure 27:
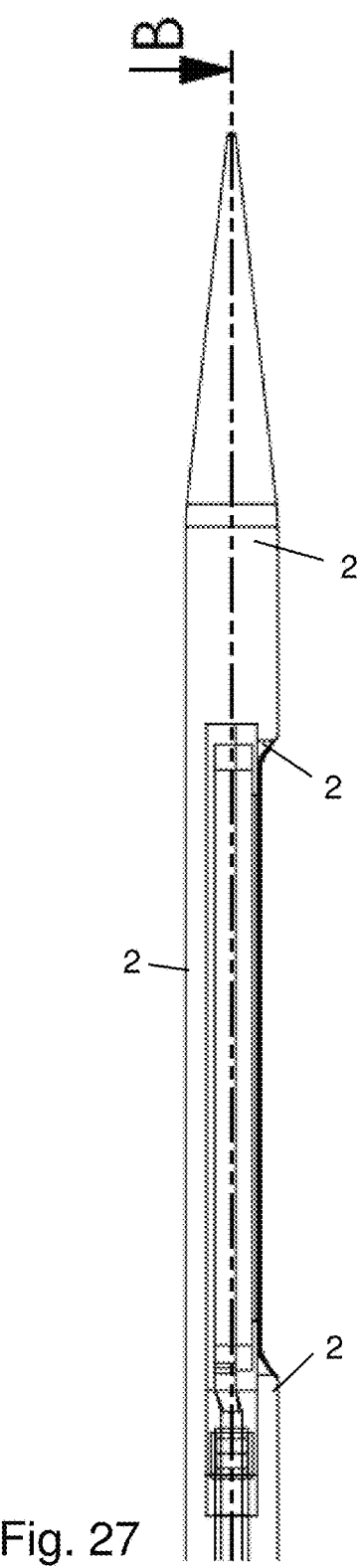
FIG. 27 shows the fluid interface device of FIG. 24 in a side elevation view.
Figure 28:
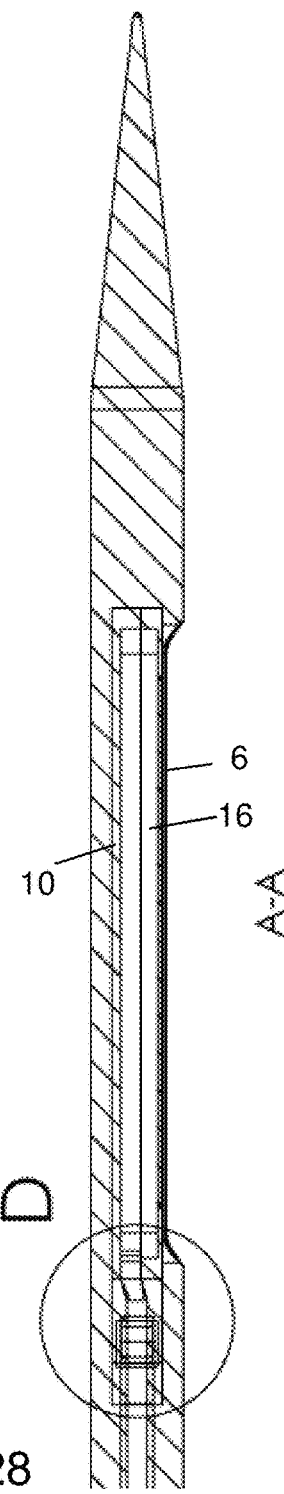
FIG. 28 shows the the fluid interface device of FIG. 24 in a sectional view according to section A-A.
Figure 29:
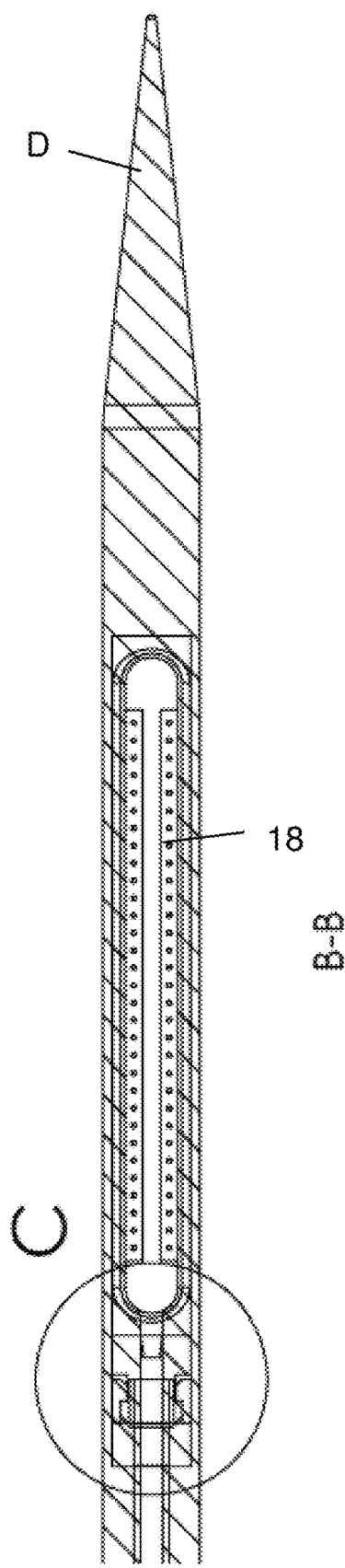
FIG. 29 shows the the fluid interface device of FIG. 24 in a sectional view according to section B-B.
Figure 30:
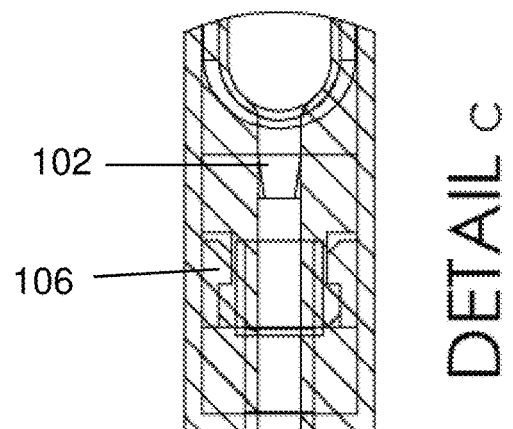
FIG. 30 shows an enlarged view of detail C of FIG. 28.
Figure 31:
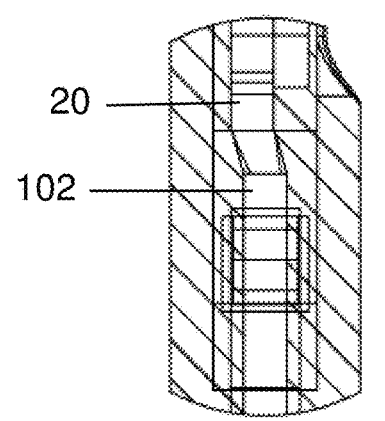
FIG. 31 shows an enlarged view of detail D of FIG. 28.
Figure 32:
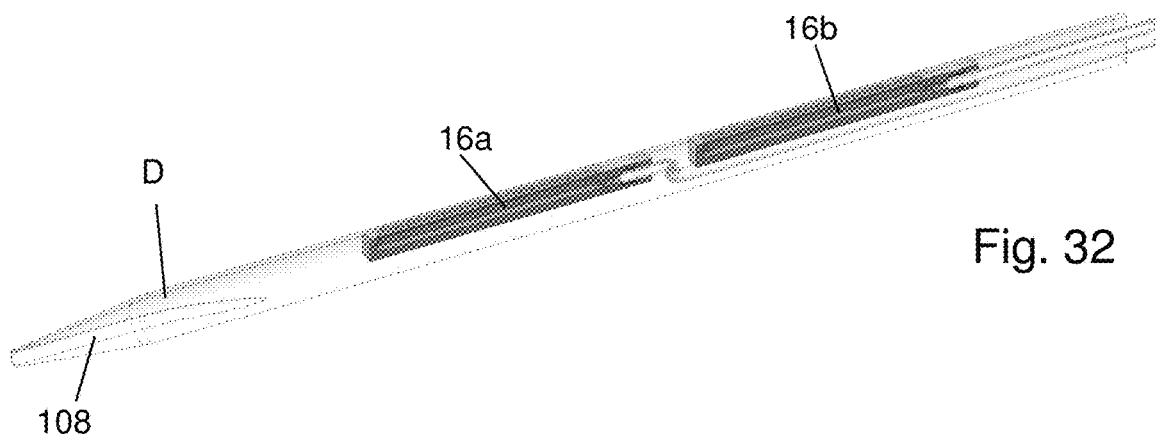
FIG. 32 shows a fifth embodiment of a fluid interface, in a partially cut away perspective view.
Figure 33:
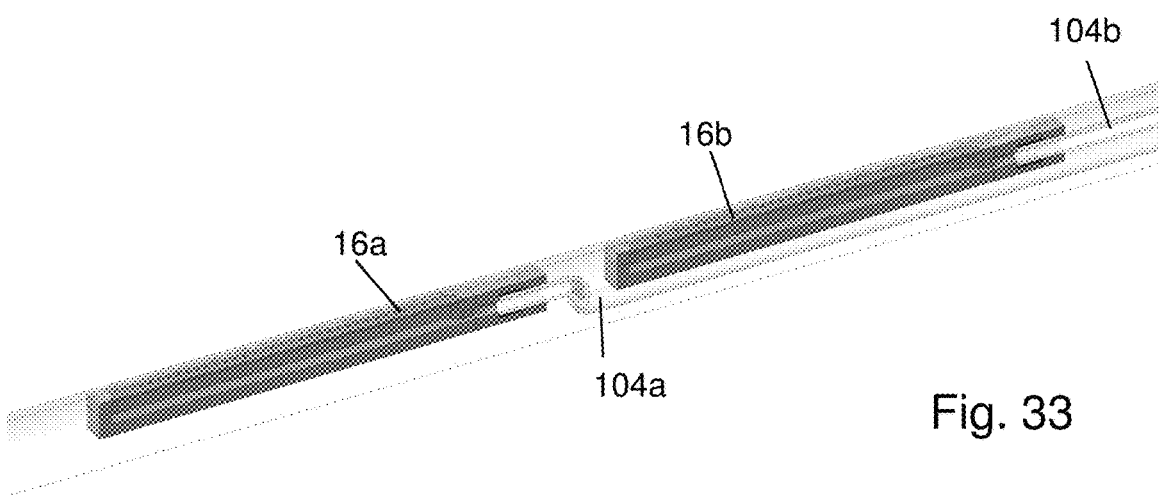
FIG. 33 shows an enlarged view of a detail of FIG. 32.
Figure 34:
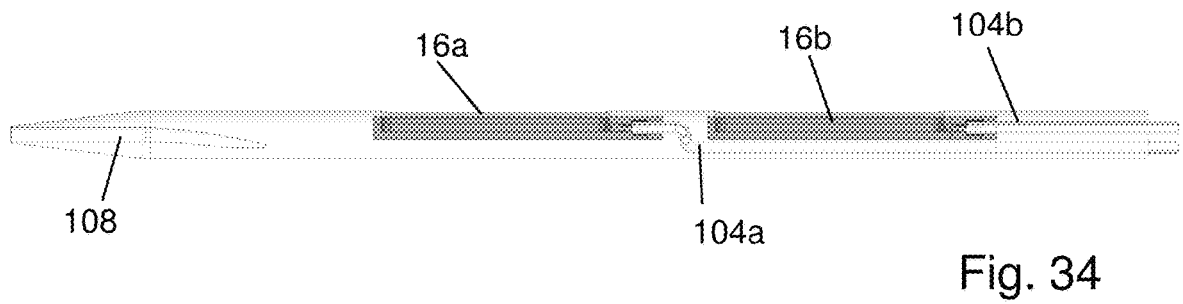
FIG. 34 shows the fluid interface device of FIG. 32 in a plan view seen from the secondary faces.
Figure 35:
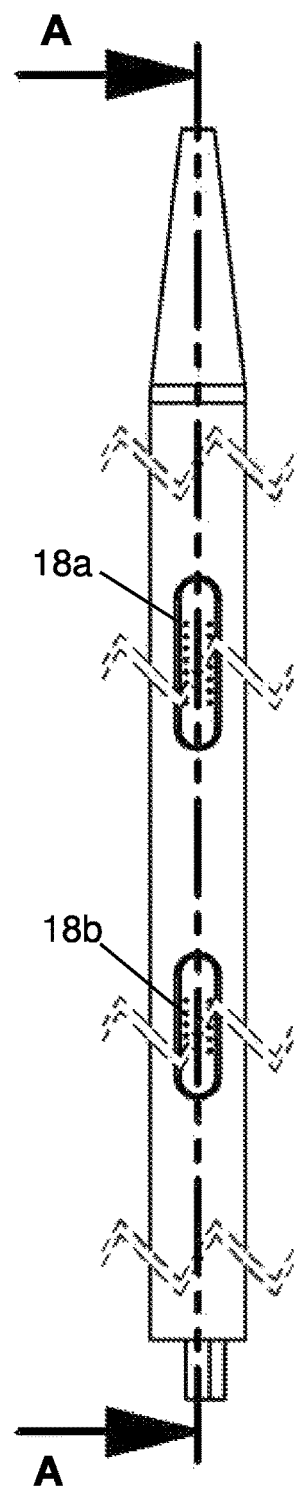
FIG. 35 shows the fluid interface device of FIG. 32 in a plan view seen from the primary face, with some longitudinal segments cut away.
Figure 36:
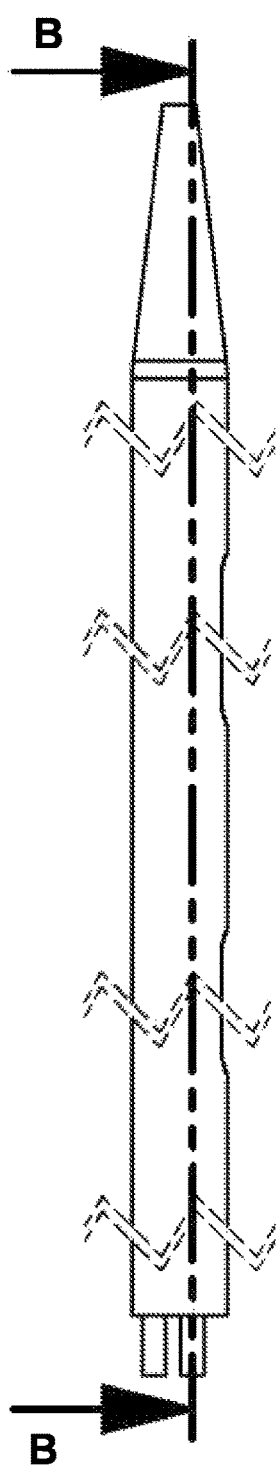
FIG. 36 shows the fluid interface device of FIG. 32 in a side elevation view, with some longitudinal segments cut away.
Figure 37:
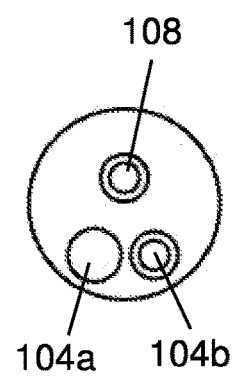
FIG. 37 shows the fluid interface device of FIG. 32 in an axial view from the proximal end.
Figures 38, 39, 40, 41:
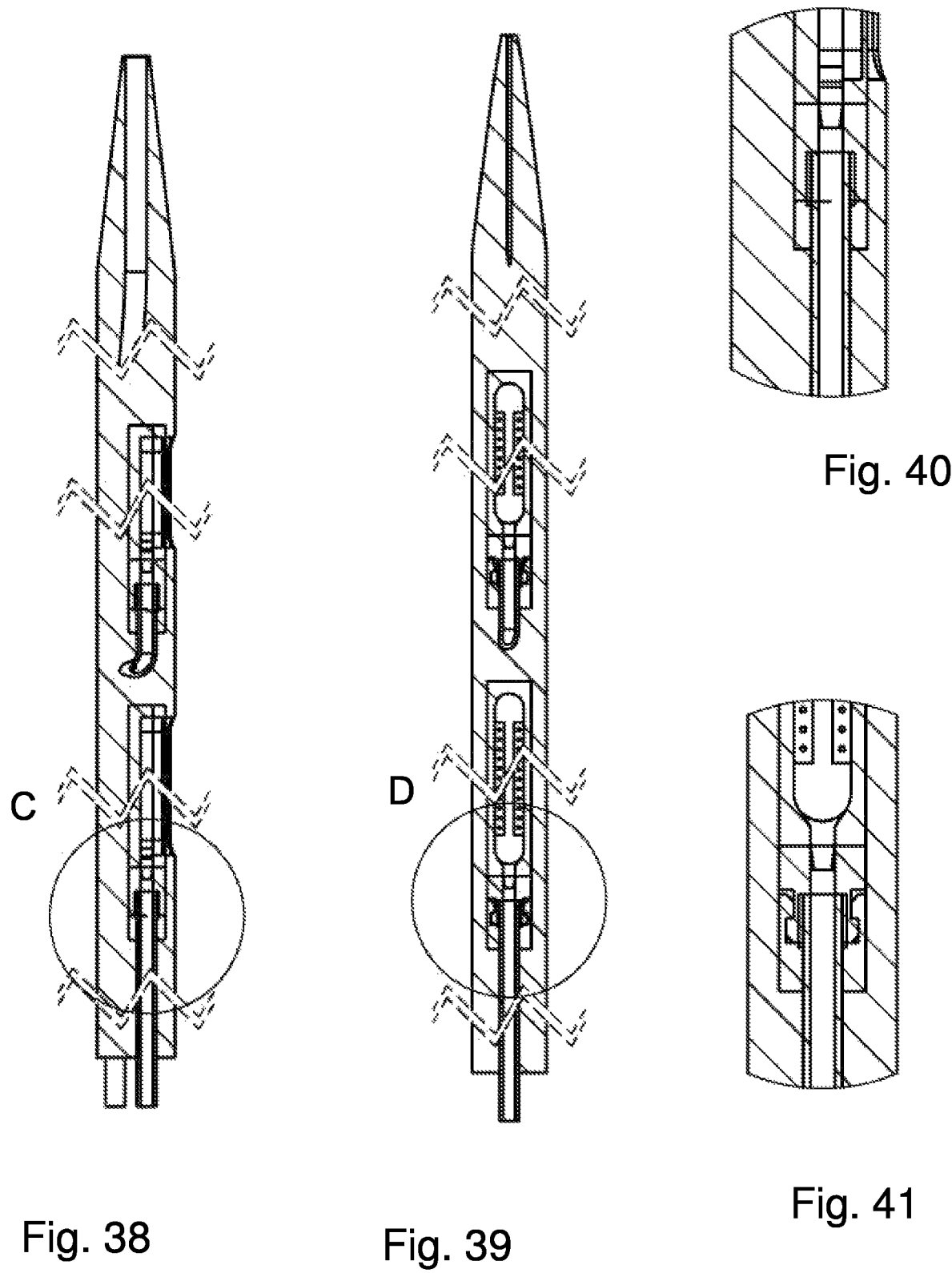
FIG. 38 shows the the fluid interface device of FIG. 32 in a sectional view according to section A-A.
FIG. 39 shows the the fluid interface device of FIG. 32 in a sectional view according to section B-B.
FIG. 40 shows an enlarged view of detail C of FIG. 38.
FIG. 41 shows an enlarged view of detail D of FIG. 38.

A further variant of the fluid interface device of the present invention is illustrated in FIG. 23. The device comprises a peripheral base element 2, which in the example shown is configured as a simple surrounding piece with an inwardly protruding flange 3. The counterplate has just one fluid port 20 for fluid delivery to and/or fluid withdrawal from the buffer volume.

In the example shown, the counterplate 10 is substantially planar. In contrast, the front platelet 6 has a peripheral protrusion zone 22 directed towards the counterplate 10 and forming a lateral wall enclosing the buffer volume 16. Both the front platelet 6 and the counterplate 14 are made of Si and/or $Si_3N_4$ and are joined to each other e.g. by anodic bonding.

A third embodiment of a fluid interface device is shown in FIGS. 24 to 31. The device is configured as an elongated body having a proximal end P, a distal end D and a lateral surface S therebetween. The front platelet 6 of the fluid transmission element 4 is disposed to form part of the lateral surface S. The distal end D of the elongated body B has a pointed shape. The embodiment of FIGS. 24 to 31 is a device wherein the buffer volume 16 comprises a single compartment being in connection with a respective microchannels array 18 and one fluid port 20. As will be seen from the figures, the fluid port 20 is arranged at the proximal side of the counterplate 10 and enters into the buffer volume 16 in a substantially longitudinal direction. This allows for a very compact construction with a small overall diameter of only about 5 mm. The front platelet 6 and the counterplate 10 are form a two-plate stack that is surrounded from the peripheral base element 2, which as seen particularly from FIG. 27, forms an outer sheath of the elongated body.

The elongated body comprises a fluid passage 102 leading from the fluid port 20 to a channel opening 104 at the proximal end of the elongated body. The proximal end is provided with means 106 for attaching a fluid supply connector to the channel opening.

FIGS. 32 to 41 show a fourth embodiment of the fluid interface device wherein the buffer volume comprises two separate compartments 16a and 16b, each compartment being in connection with a respective microchannels array 18a, 18b and a respective fluid port 20a, 20b. The two compartments are arranged at the same side of the elongated body B. As shown in the figures, this arrangement requires that the fluid passage 102a leading from the more distal compartment 16a to the channel opening 104a passes in a laterally displaced manner along the more proximal compartment 16b.

In the embodiment shown in FIGS. 32 to 41, the elongated body B is provided with a longitudinal passage 108 extending from the distal end D to the proximal end E. The passage is configured as a smooth channel without sharp bends and has a diameter of typically 0.5 mm suitable for accommodating a guide wire as generally used in catheter type interventions.

Figure 42:
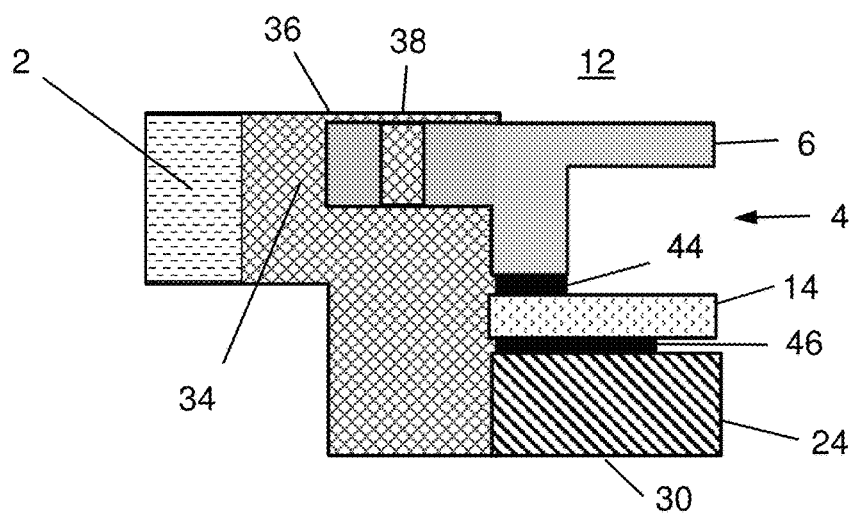
FIG. 42 shows a sixth embodiment of a fluid interface device, in a schematic sectional view.

The basic structure of a fluid interface device suitable for implantation in a tubular structure such as an arteriovenous shunt is illustrated in FIG. 42. For this purpose the peripheral base element 2 is formed as a wall section of a tubular segment to be described in more detail further below. In order to form a compact, reliable and medium tight connection between the base element 2 and the fluid interface structure 4, an arrangement as shown in FIG. 42 can be used. Such arrangement comprises a ridge structure 34 surrounding the fluid transmission element 4 and sealingly connecting the latter with the base element 2. The ridge structure 34 is made of a biocompatible thermoplastic polymer formed around the fluid transmission element 4 by injection molding. In order to promote a good adhesion of the ridge structure 34 with the fluid transmission element 4, the front platelet 6 has an outwardly protruding collar 36 provided with a plurality of holes 38. As shown in FIG. 42, the injection molded material of the ridge structure 34 is disposed around the collar 36 and within the holes 38, which provides a form-locking effect. It will be understood that instead of holes the collar could be provided with other types of locking structures such as recesses and protrusions.

In the example shown in FIG. 42 the peripheral base element 2 is sealingly connected to the ridge structure 34 by a suitable joining method such as ultrasonic welding. It will be understood that this convenient joining method requires that the thermoplastic polymer of the ridge structure 34 and that of the peripheral base element 2 are either the same or compatible to each other.

However, in other embodiments the ridge structure 34 and the peripheral base element 2 are integrally formed of one and the same thermoplastic polymer.

As also shown in the schematic representation of FIG. 42, the front platelet 6 and the counterplate 14 are joined to each other in a first contacting zone 44 formed by anodic bonding. Further, the counterplate 14 and the spacer 24 are joined to each other in a second contacting zone 46 by means of a suitable adhesive.

A convenient manner of assembling the exemplary device of FIG. 42 for the case that the ridge structure 34 and the peripheral base element 2 are integrally formed may be summarized as follows:

- place a previously assembled fluid transmission element 4 onto a corresponding holder with the front platelet 6 downwards
- stack the spacer element 24 onto the counterplate 14 and join with suitable adhesive 46
- form the ridge structure 34 and peripheral base element 2 by injection molding around the fluid transmission element 4.

Figure 43:
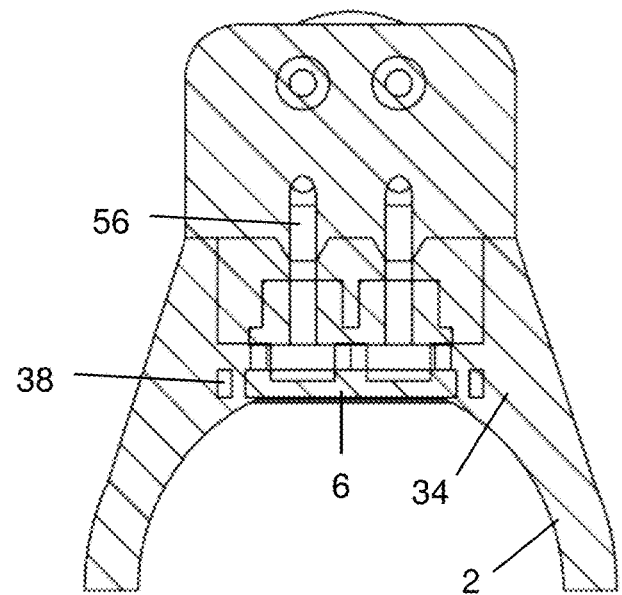
FIG. 43 shows the arrangement of FIG. 16 in a sectional view according to section C-C.
Figure 44:
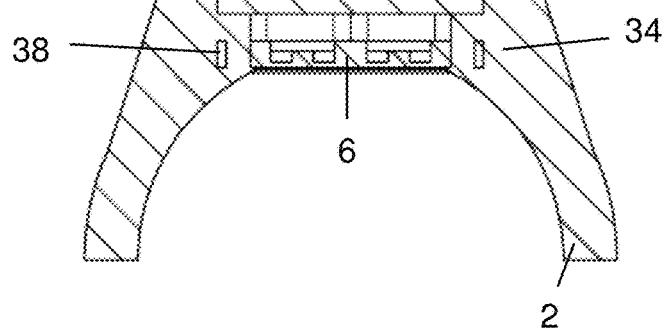
FIG. 44 shows the arrangement of FIG. 16 in a sectional view according to section D-D.
Figure 45:
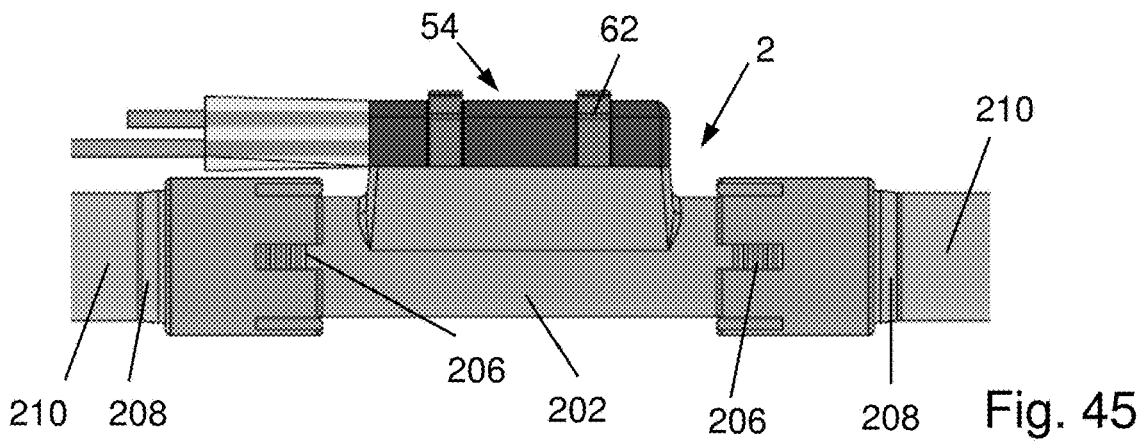
FIG. 45 shows another fluid interface device with an integrally formed tubular section, including the front platelet and counterplate of FIG. 8 and a fluid supply connector attached thereto, in a side elevation view.
Figure 46:
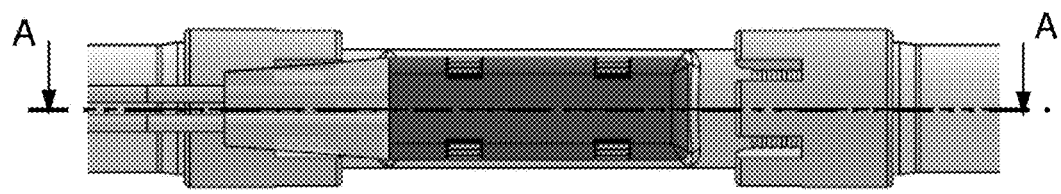
FIG. 46 shows the arrangement of FIG. 45 in a plan view.
Figure 47:
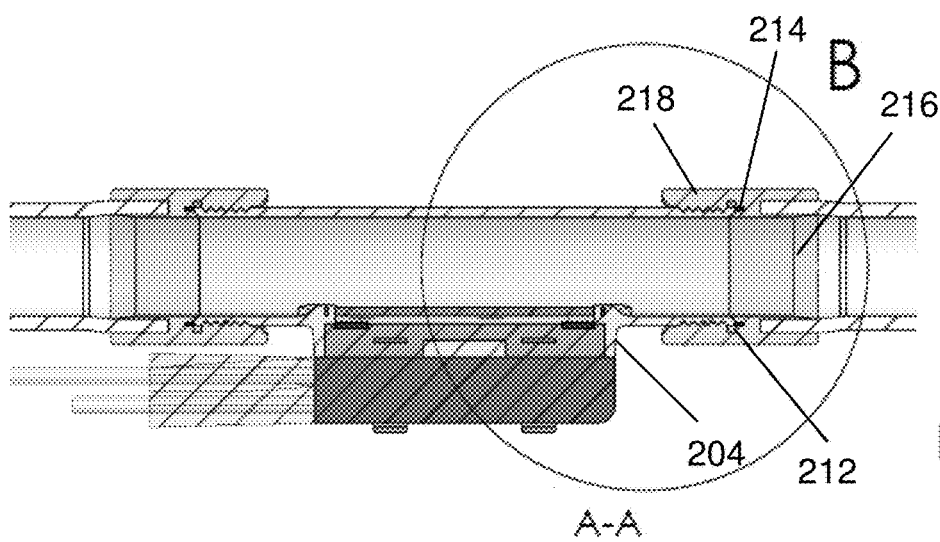
FIG. 47 shows the arrangement of FIG. 45 in a sectional view according to section A-A.
Figure 48:
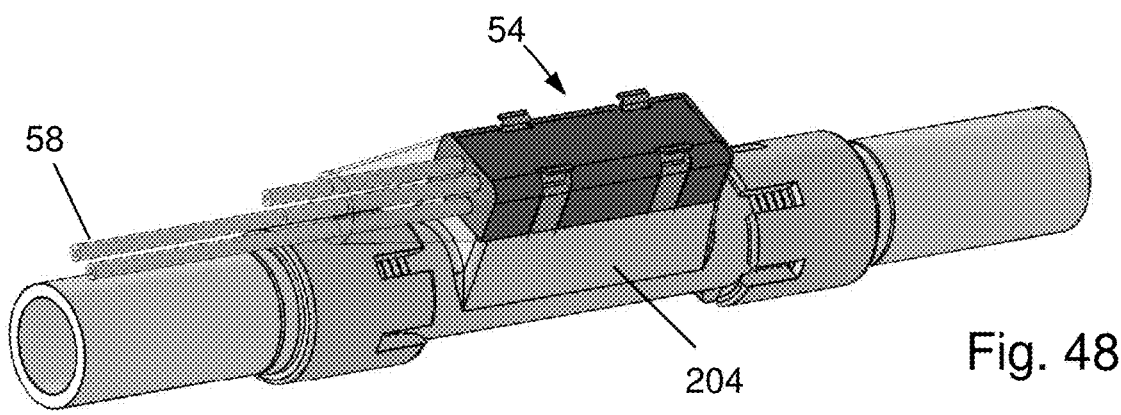
FIG. 48 shows the arrangement of FIG. 45 in a perspective view.
Figure 49:
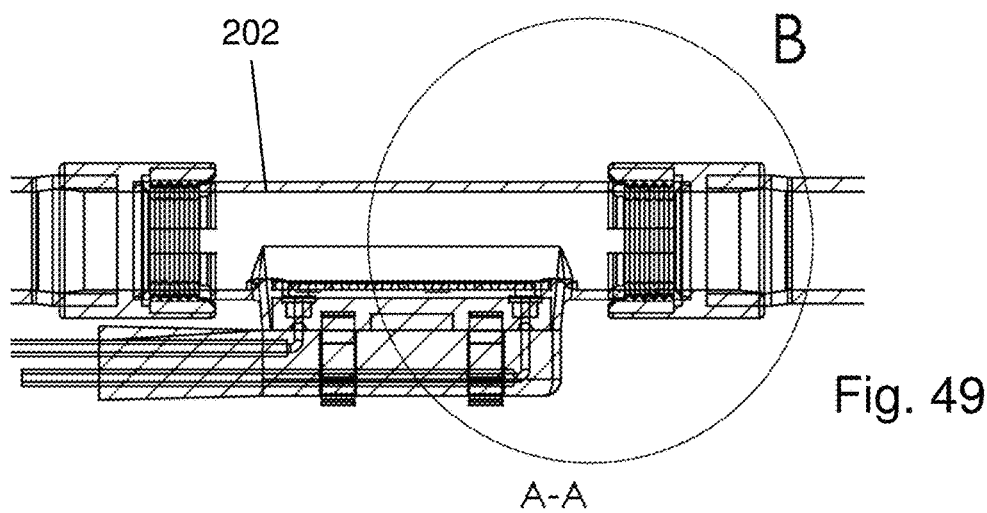
FIG. 49 shows a more detailed rendition of FIG. 47.
Figure 50:
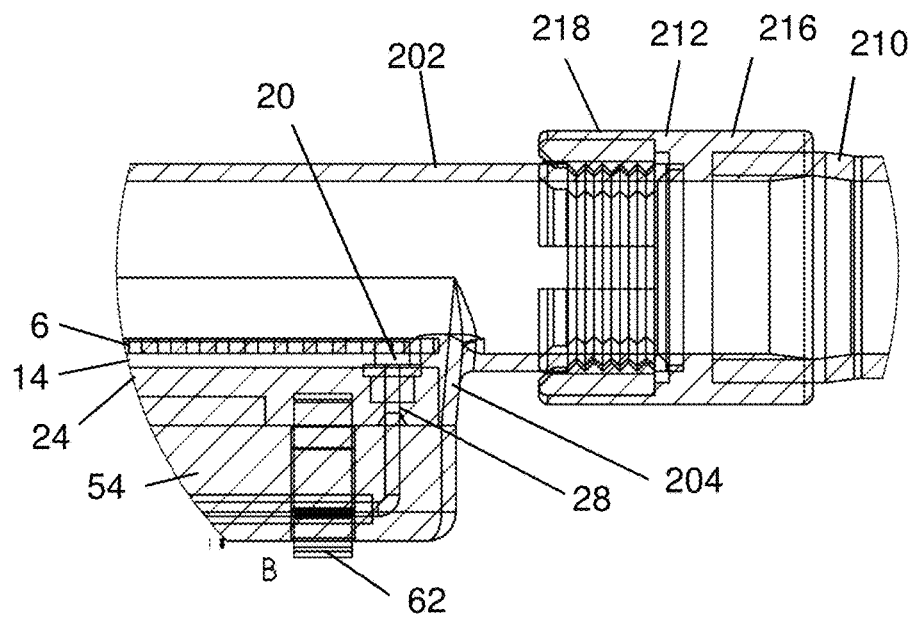
FIG. 50 shows an enlarged view of the portion marked as "B" in FIG. 49.

Further details of an embodiment of the fluid interface device suitable for implantation in a blood vessel are illustrated in FIGS. 4 to 16, and in FIGS. 43 and 44. Features corresponding to those in the embodiments explained above are generally denoted with the same reference numerals as above.

FIGS. 12 to 16 and 43 and 44 show a fluid interface with a fluid supply connector 54 attached thereto. It should be noted particularly in relation to FIGS. 14 and 15 and also FIGS. 43 and 44 that the peripheral base element 2 could also be integrally formed with an entire tubular section of the device. In that case the feature denoted as 2 in the lower part of FIGS. 17 and 18 would actually continue downwards to form a substantially circular closed section.

As illustrated in FIGS. 43 and 44, the ridge structure 34 and the peripheral base element 2 are formed having a concave cross section dimensioned in accordance with the cross section of a blood vessel into which the entire device can be implanted.

Comparison of FIG. 44 with FIG. 18 furthermore shows that the peripheral base element 2, the ridge structure 34 and also the covering part 40 which in the embodiment of FIG. 18 is a separate component, are integrally formed in the embodiment of FIG. 44.

A further embodiment particularly suitable for connection to a tubular structure such as an arteriovenous shunt is shown in FIGS. 45 to 50. The arrangement generally comprises a peripheral base element 2 circumferentially surrounding a fluid transmission element 4 consisting of a front platelet 6 with a primary face 8 and a secondary face 10 opposed thereto, the primary face being in contact with a patient's body fluid region 12 when the device is implanted in the patient. The fluid transmission element further comprises a counterplate 14 sealingly stacked against the secondary face of the front platelet and forming a buffer volume 16 therebetween. The front platelet comprises an array of microchannels 18 defining a fluid passage between the buffer volume and the primary face. The peripheral base element is configured as a wall section of an integrally formed tubular segment 202 which comprises an integrally formed ridge structure 204 providing a sealing lateral closure of the layered fluid transmission element 4.

The tubular segment 202 is provided at both ends thereof with connecting means 206 for medium tight coupling to correspondingly equipped ends 208 of a tubular structure 210 such as an arteriovenous shunt grafted to a patient. In the example shown the connecting means are configured as end sections of the tubular segment 202 provided with ratchet-like external projections 206 and with a terminal collar 212 for receiving an O-ring 214. As will also be seen from the figures, the ends 208 of the grafted tubular structure 210 are provided with a crimped on ferrule 216 which has an axially forward projecting ring bracket 218 cooperating with the connectors 206 and having a front surface serving to sealingly abut against O-ring 214. In the example shown, the connection can be released by applying a radially outward force on the ring bracket 218.

Figure 51:
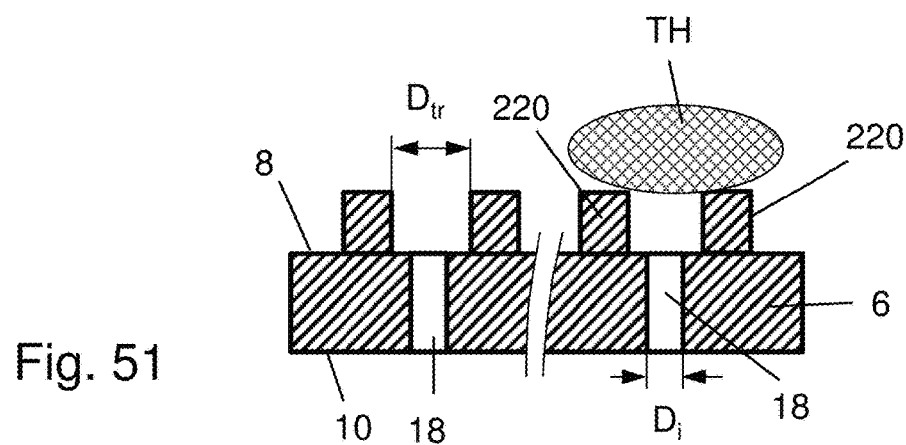
FIG. 51 shows a vertical section through a front platelet provided with guard elements, partially cut away.

FIG. 51 shows a vertical section through a front platelet 6 provided with guard elements 220. As seen from this schematic rendering, two microchannels 18 a fluid communication path between the primary face 8 and the secondary face 10. The channels have an opening with an inner diameter $d_i$, which is selected in the range of 0.6 to 2 μm. The guard elements are formed in such manner as to define a transversal limitation $D_{tr}$ over each microchannel exit, the transversal limitation being larger than the microchannel opening and being selected in the range of 2 to 4 μm. The guard elements can be configured as pillars, i.e. as stub-like protrusions with an outer diameter $d_o$ or as mutually parallel ribbons with a width $d_o$ and a length that can extend across the entire primary face. As seen from the figure, the transversal limitation $D_{tr}$ defined by the guard elements forms a stop for a thrombocyte TH while still allowing fluid to flow through the cavity formed between the thrombocyte and the primary face 8.

What I claim is:

1. A fluid interface device for delivering fluid to and/or withdrawing fluid from a body of a patient, the device comprising:
    a peripheral base element;
    a fluid transmission element forming a central portion of the device and being sealingly connected to the peripheral base element which is circumferentially arranged around the fluid transmission element, the fluid transmission element comprising a front platelet with a primary face and a secondary face opposed to the primary face, the primary face being in contact with a patient's body fluid region when the device is implanted into the body of the patient, the fluid transmission element further comprising a counterplate sealingly stacked against the secondary face of the front platelet and forming a buffer volume therebetween;
    the front platelet comprising at least one array of microchannels defining a fluid passage between the buffer volume and the primary face, each of the microchannels is a circular microchannel or a non-circular microchannel, wherein each of the circular microchannels has a diameter of 0.6 μm to 2 μm and each of the non-circular microchannels has a smallest transversal size of 0.6 μm to 2 μm;
    the fluid transmission element having at least one fluid port for fluid delivery to and/or fluid withdrawal from the buffer volume,
    wherein the primary face is provided with guard elements protruding with respect to a plane defined by microchannel exits located in the primary face, the guard elements being formed in such manner as to define at least one transversal limitation over each microchannel exit, the transversal limitation being larger than, for each of the circular microchannels, the diameter of each of the circular microchannels and, for each of the non-circular microchannels, the smallest transversal size of each of the non-circular microchannels and being in the range of 2 μm to 4 μm.

2. The fluid interface device according to claim 1, wherein the at least one fluid port comprises at least two fluid ports.

3. The fluid interface device according to claim 2, wherein each fluid port is arranged in the counterplate.

4. The fluid interface device according to claim 1, wherein the front platelet is made of Si and/or $Si_3N_4$, and wherein the counterplate is made of glass.

5. The fluid interface device according to claim 1, wherein the front platelet and the counterplate are joined to each other by anodic bonding.

6. The fluid interface device according to claim 1, wherein the fluid transmission element and the base element are sealingly connected to each other via a ridge structure surrounding the fluid transmission element, the ridge structure being made of a biocompatible thermoplastic formed around the fluid transmission element by injection molding.

7. The fluid interface device according to claim 6, wherein the peripheral base element is sealingly connected to the ridge structure by injection molding thereon a covering part or by ultrasonic welding.

8. The fluid interface device according to claim 6, wherein the peripheral base element is formed as a foamed pad of a thermoplastic fluoropolymer which is suitable for implantation in a patient's blood vessel wall, and wherein the injection molded ridge structure is formed as a non-foamed body of said thermoplastic fluoropolymer.

9. The fluid interface device according to claim 1, wherein the peripheral base element is formed as a rigid frame structure suitable for fixation to an osseous structure of a patient.

10. The fluid interface device according to claim 1, which is configured as an elongated body having a proximal end, a distal end and a lateral surface therebetween, the front platelet of the fluid transmission element being disposed to form part of the lateral surface.

11. The fluid interface device according to claim 10, wherein the distal end of the elongated body has a pointed shape.

12. The fluid interface device according to claim 10, wherein the elongated body is provided with a longitudinal passage extending from the distal end to the proximal end.

13. The fluid interface device according to claim 10, wherein the peripheral base element forms an outer sheath of the elongated body.

14. The fluid interface device according to claim 10, wherein the front platelet and the counterplate are made of Si and/or $Si_3N_4$.

15. The fluid interface device according to claim 10, wherein the buffer volume comprises a single compartment being in connection with a respective microchannel array and one of the at least one fluid port.

16. The fluid interface device according to claim 10, wherein the at least one fluid port comprises two fluid ports and wherein the buffer volume comprises a single compartment being in connection with a respective microchannel array and the two fluid ports.

17. The fluid interface device according to claim 10, wherein the buffer volume comprises two separate compartments, each compartment being in connection with a respective microchannels array and a respective fluid port.

18. The fluid interface device according to claim 17, wherein the two separate compartments are arranged at one side of the elongated body.

19. The fluid interface device according to claim 10, wherein the at least one fluid port comprises two fluid ports and wherein the buffer volume comprises two separate compartments, each compartment being in connection with a respective microchannels array and the two fluid ports.

20. The fluid interface device according to claim 10, wherein the elongated body comprises for each fluid port of the at least one fluid port a fluid passage leading to a channel opening at the proximal end of the elongated body.

21. The fluid interface device according to claim 20, wherein said proximal end is provided with means for attaching a fluid supply connector to each one of said channel openings.

22. The fluid interface device according to claim 1, wherein the peripheral base element is configured as a wall section of a tubular segment suitable for containing a patient's body fluid.

23. The fluid interface device according to claim 22, wherein the fluid transmission element and the base element are sealingly connected to each other by means of a ridge structure surrounding the fluid transmission element, the ridge structure being made of a biocompatible thermoplastic formed around the fluid transmission element by injection molding, and wherein the peripheral base element is integrally formed on the tubular segment which is also made of the biocompatible thermoplastic.

24. The fluid interface device according to claim 22, wherein the tubular segment is provided at both ends thereof with means for connecting to a patient's systemic circuit.

25. A system for delivering fluid to and/or withdrawing fluid from a patient's body region, the system comprising the fluid interface device according to claim 1, fluid storage means and fluid transfer means for controlled fluid delivery to and fluid withdrawal from the buffer volume via the at least one fluid port, the system being configured to be able to perform at least the following steps according to a pre-defined step sequence:
   a) running flushing medium through the buffer volume;
   b) running flushing medium through the at least one microchannels array;
   c) withdrawing patient's body fluid through the at least one microchannels array; and
   d) delivering a therapeutic agent to the patient.

26. The system according to claim 25, wherein the fluid transfer means are configured as transdermal tubing.

27. The system according to claim 25, wherein the fluid transfer means comprise:
   a subcutaneously implantable injection port having at least one injection chamber, each injection chamber having an upper inlet opening covered by a pierceable septum and an exit opening;
   at least one fluid transfer line having a first and a second end connectable at the first end to said exit opening and connectable at the second end to a corresponding fluid port of said fluid interface device.

28. The system according to claim 25, further comprising means for establishing a continuous or intermittent flow of supply medium through the buffer volume, whereby a fraction of supply medium is delivered to the patient through the fluid transmission element.

29. A method of operating the system according to claim 25, in which method a flushing medium is delivered to the buffer volume so as to maintain an overpressure relative to a base pressure in the patient's body region when the system is not withdrawing patient's body fluid or delivering a therapeutic agent to the patient, thereby preventing any flow from the patient's body region through the microchannels into the buffer volume.

30. A method for delivering fluid to and/or withdrawing fluid from a patient's body region, comprising:
 providing the fluid interface device of claim 1, which is part of a system also comprising fluid storage means and fluid transfer means for controlled fluid delivery to and fluid withdrawal from the buffer volume via the at least one fluid port,
 delivering a flushing medium to the buffer volume, whereby an overpressure relative to a base pressure in the patient's body region when the system is not withdrawing patient's body fluid or delivering a therapeutic agent to the patient is maintained and, thereby preventing any flow from the patient's body region through the microchannels into the buffer volume, and
 withdrawing the fluid/the patient's body fluid from the patient's body region through the at least one microchannels array and/or delivering the fluid/the therapeutic agent to the patient.

31. A fluid interface device for delivering fluid to and/or withdrawing fluid from a body of a patient, the device comprising:
 a peripheral base element;
 a fluid transmission element forming a central portion of the device and being sealingly connected to the peripheral base element which is circumferentially arranged around the fluid transmission element, the fluid transmission element comprising a front platelet with a primary face and a secondary face opposed to the primary face, the primary face being in contact with a patient's body fluid region when the device is implanted into the body of the patient, the fluid transmission element further comprising a counterplate sealingly stacked against the secondary face of the front platelet and forming a buffer volume therebetween;
the front platelet comprising at least one array of microchannels defining a fluid passage between the buffer volume and the primary face, each of the microchannels is a circular microchannel or a non-circular microchannel, wherein each of the circular microchannels has a diameter of 0.2 µm to 10 µm and each of the non-circular microchannels has a smallest transversal size of 0.2 µm to 10 µm;
 the fluid transmission element having at least one fluid port for fluid delivery to and/or fluid withdrawal from the buffer volume, wherein
 (i) the counterplate is substantially planar and wherein the buffer volume is enclosed within a peripheral protrusion zone of the secondary face of the front platelet, and/or
 (ii) the buffer volume comprises at least two separate compartments, each compartment being in connection with a respective microchannel array and the at least one fluid port.

32. The fluid interface device according to claim 31, wherein the buffer volume comprises the at least two separate compartments of (ii).

33. The fluid interface device according to claim 31, wherein the counterplate is substantially planar and wherein the buffer volume is enclosed within the peripheral protrusion zone of the secondary face of the front platelet.

34. A fluid interface device for delivering fluid to and/or withdrawing fluid from a body of a patient, the device comprising:
 a peripheral base element;
 a fluid transmission element forming a central portion of the device and being sealingly connected to the peripheral base element which is circumferentially arranged around the fluid transmission element, the fluid transmission element comprising a front platelet with a primary face and a secondary face opposed to the primary face, the primary face being in contact with a patient's body fluid region when the device is implanted into the body of the patient, the fluid transmission element further comprising a counterplate sealingly stacked against the secondary face of the front platelet and forming a buffer volume therebetween;
the front platelet comprising at least one array of microchannels defining a fluid passage between the buffer volume and the primary face, each of the microchannels is a circular microchannel or a non-circular microchannel, wherein each of the circular microchannels has a diameter of 0.2 µm to 10 µm and each of the non-circular microchannels has a smallest transversal size of 0.2 µm to 10 µm;
 the fluid transmission element having at least two fluid ports for fluid delivery to and/or fluid withdrawal from the buffer volume, each fluid port being arranged in the counterplate, the fluid interface device further comprising a spacer element made of a thermoplastic polymer, the spacer element having a first spacer face that is adhesively connected to an external face of the counterplate, the spacer element comprising traversing channels connecting the first spacer face and a second spacer face, each traversing channel being arranged to form a passage between one of the fluid ports and a corresponding channel opening at the second spacer face.

35. The fluid interface device according to claim 34, further comprising a fluid supply connector and means for releasably attaching the fluid supply connector to the spacer element, the fluid supply connector comprising connector channels each leading from a lateral entrance port to an exit port coinciding with a channel opening at the second spacer face when the fluid supply connector is attached to the spacer element.

36. The fluid interface device according to claim 35, wherein each one of said connector channels is formed as a pair of grooves in adjacent faces of mutually contacted connector parts.

37. The fluid interface device according to claim 34, further comprising a fluid supply connector attached to the spacer element, the fluid supply connector comprising connector channels each leading from an entrance port to an exit port coinciding with a channel opening at the second spacer face, the fluid supply connector being configured as a sealing mass that encapsulates the spacer element and the fluid transmission element and furthermore forms the peripheral base element.

* * * * *